US009977867B2

(12) United States Patent  
Greene

(10) Patent No.: US 9,977,867 B2  
(45) Date of Patent: May 22, 2018

(54) METHODS FOR IMPROVING THE CLINICAL OUTCOME OF PATIENT CARE AND FOR REDUCING OVERALL HEALTH CARE COSTS

(71) Applicant: MedEncentive, LLC, Oklahoma City, OK (US)

(72) Inventor: Jeffrey C. Greene, Norman, OK (US)

(73) Assignee: MedEncentive, LLC, Oklahoma City, OK (US)

( * ) Notice: Subject to any disclaimer, the term of this patent is extended or adjusted under 35 U.S.C. 154(b) by 389 days.

(21) Appl. No.: 14/923,043

(22) Filed: Oct. 26, 2015

(65) Prior Publication Data

US 2016/0042132 A1     Feb. 11, 2016

Related U.S. Application Data

(63) Continuation of application No. 13/492,441, filed on Jun. 8, 2012, now Pat. No. 9,171,285, which is a (Continued)

(51) Int. Cl.
    *G06F 19/00*     (2018.01)
    *G06Q 10/08*     (2012.01)
    (Continued)

(52) U.S. Cl.
    CPC .......... *G06F 19/328* (2013.01); *G06F 19/322* (2013.01); *G06F 19/34* (2013.01);
    (Continued)

(58) Field of Classification Search
    CPC ...... G06F 19/328; G06F 19/322; G06F 19/34; G06Q 10/087; G06Q 10/10; G06Q 30/0207; G06Q 50/20; G06Q 50/22
    See application file for complete search history.

(56) References Cited

U.S. PATENT DOCUMENTS 4,491,725 A     1/1985    Pritchard
5,947,747 A     9/1999    Walker et al.
(Continued)

OTHER PUBLICATIONS

Web officials make case for Internet health advice. Brian Reald Washington Post. Journal-Gazett, Ft. Wayne, Ind: Jul. 2, 2002. p. 1.D.

*Primary Examiner* — Linh Giang Le
(74) *Attorney, Agent, or Firm* — Lawrence F. Grable PLLC

(57) ABSTRACT

System and method for reducing healthcare costs by improving care and encouraging healthy behaviors. A web-based or telephonic program using health plan sponsor funded financial incentives, offered to patients and providers for declaring or demonstrating adherence or providing a reason for non-adherence to performance standards. Financial incentives are contingent upon patient's and provider's agreement to allow the other to confirm or acknowledge the other's declaration or demonstration of adherence or non-adherence reason. Combining financial incentives with a set of checks and balances motivates participation in the program and adherence to the performance standards. Performance standards include evidence-based treatment guidelines, information therapy, wellness and prevention solutions, care management, and other methods proven to control costs by improving behaviors and healthcare. The system and method achieves improved health and more affordable healthcare by aligning the interests of providers, patients/consumers, and health plan sponsors in a win-win-win arrangement.

20 Claims, 22 Drawing Sheets

Related U.S. Application Data continuation-in-part of application No. 13/166,467, filed on Jun. 22, 2011, which is a continuation of application No. 11/596,305, filed as application No. PCT/US2005/015791 on May 6, 2005, which is a continuation-in-part of application No. 10/841,240, filed on May 6, 2004.

(51) Int. Cl.
  G06Q 10/10 (2012.01)
  G06Q 50/22 (2018.01)
  G06Q 30/02 (2012.01)
  G06Q 50/20 (2012.01)

(52) U.S. Cl.
  CPC ........... *G06Q 10/087* (2013.01); *G06Q 10/10* (2013.01); *G06Q 30/0207* (2013.01); *G06Q 50/20* (2013.01); *G06Q 50/22* (2013.01)

(56) References Cited

U.S. PATENT DOCUMENTS

| | | | |
|---|---|---|---|
| 6,161,095 A | 12/2000 | Brown | |
| 6,208,973 B1 | 3/2001 | Boyer et al. | |
| 6,317,700 B1 | 11/2001 | Bagne | |
| 6,558,929 B2 | 5/2003 | Thum et al. | |
| 7,076,437 B1 | 7/2006 | Levy | |
| 7,389,245 B1 | 6/2008 | Ashford et al. | |
| 2001/0041992 A1 | 11/2001 | Lewis et al. | |
| 2002/0007285 A1 | 1/2002 | Rappaport | |
| 2002/0010597 A1 | 1/2002 | Mayer et al. | |
| 2002/0072933 A1 | 6/2002 | Vonk et al. | |
| 2002/0091546 A1 | 7/2002 | Christakis | |
| 2002/0138306 A1* | 9/2002 | Sabovich | G06Q 10/10 705/3 |
| 2002/0169638 A1 | 11/2002 | Rodriguez-Cue | |
| 2002/0169771 A1 | 11/2002 | Melmon et al. | |
| 2002/0194022 A1 | 12/2002 | Comite | |
| 2002/0194025 A1 | 12/2002 | Notelovitz | |
| 2003/0009355 A1 | 1/2003 | Gupta | |
| 2003/0028399 A1 | 2/2003 | Davis et al. | |
| 2003/0163352 A1* | 8/2003 | Surpin | G06Q 10/10 705/2 |
| 2003/0195838 A1* | 10/2003 | Henley | G06F 19/327 705/37 |
| 2004/0044546 A1 | 3/2004 | Moore | |
| 2004/0176979 A1 | 9/2004 | Gottlieb et al. | |

\* cited by examiner

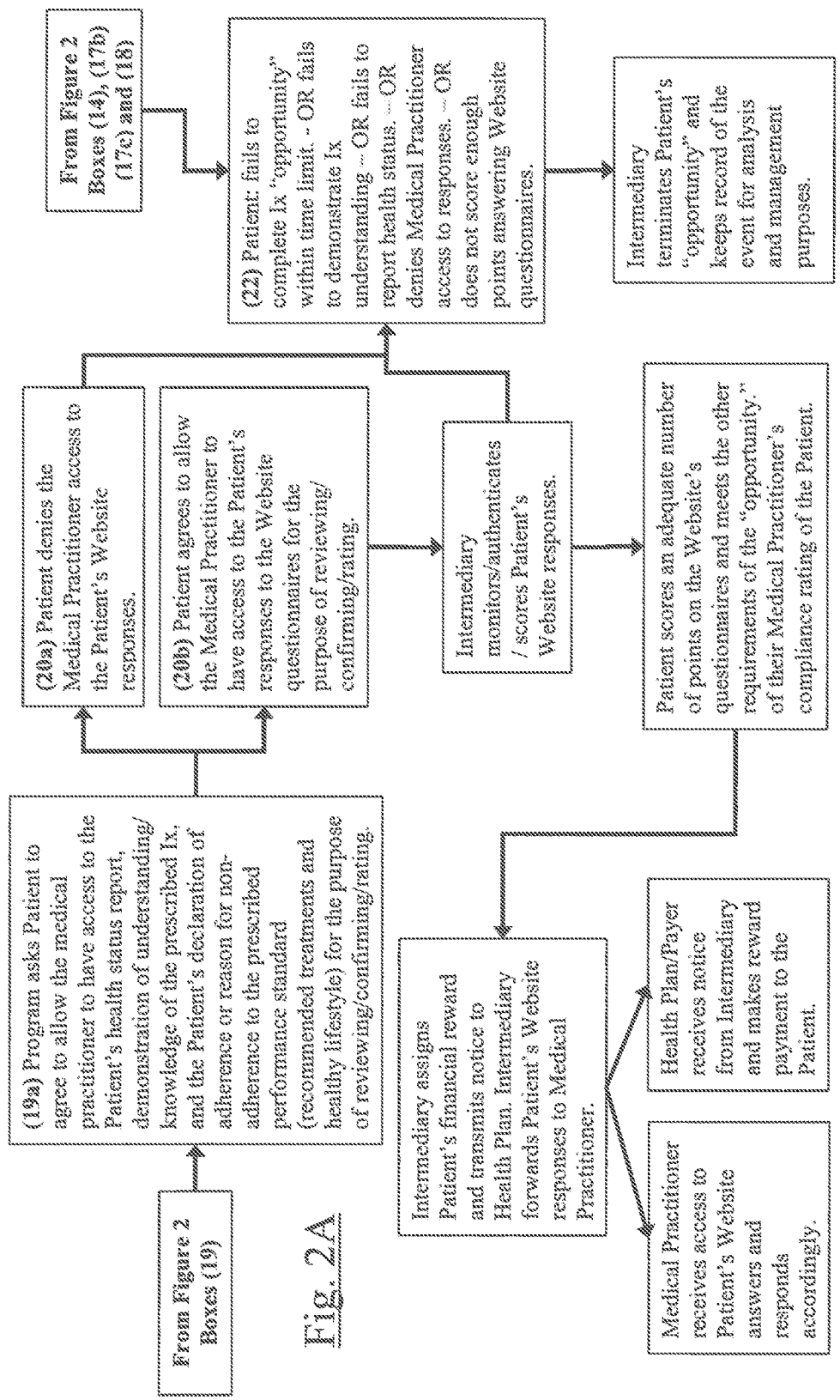

http://www.intermediary.com/realtime/step1.aspx

Web Browser Menu Bar

Intermediary Website Banner

Product Description | News & Press Releases | Providers | Patients | Employers | Administrators Step 1

Point of Service Initiated Ix Application

This application is designed to offer physicians access to evidence-based medicine guidelines and the ability to prescribe Ix (information therapy) to their patients on a real-time basis. Simply follow the easy five step process beginning with the member (patient) identification number below. Then click the "Continue" link. (If the patient's member identification is not found on their card try their social security number or scroll for their name, below.)

MemberID: [_____] Continue or

Last Name: [_____] Continue

For help or to make suggestions Contact Intermediary.

Web Browser Status Bar

Fig. 5 http://www.intermediary.com/realtime/step3.aspx

Web Browser Menu Bar

Intermediary Website Banner

Product Description | News & Press Releases | Providers | Patients | Employers | Administrators Go Back / Log Out Point of Service Initiated Ix Application*

Step 3

You now need to enter the patient's primary diagnosis followed by any secondary diagnoses You must enter at least the first three digits (alpha-numeric) of the diagnosis code to perform a numeric search.

If you know the numeric code, enter it here: ☐☐☐●☐☐ or

If you need to perform an alphanumeric search, Click Here.

or

Select from a list of your most frequently treated diagnoses, Click Here.

or

Select from a list of this patient's diagnoses, Click Here.

* Real-Time Version
For help or to make suggestions Contact Intermediary.

Web Browser Status Bar

Fig. 6 http://www.intermediary.com/realtime/step3.aspx

Web Browser Menu Bar

Intermediary Website Banner

Product Description | News & Press Releases | Providers | Patients | Employers | Administrators Go Back / Log Out Point of Service Initiated Ix Application You have added the following diagnosis.
You may list up to 4 diagnoses by clicking
the "Add Another Diagnosis" link, below.
When done selecting diagnoses, click the
"Continue to the Next Step" link, below.

Step 3

You may re-order
these codes by
highlighting a code
and clicking the
"up-down" arrows Selected Diagnoses Primary Diagnosis:    1st Diagnosis
Secondary Diagnosis:  2nd Diagnosis (EBM)      Up
Tertiary Diagnosis:   3rd Diagnosis            Down You may either:
Add Another Diagnosis or Continue to the Next Step For help or to make suggestions Contact Intermediary.

Web Browser Status Bar

Fig. 7 http://www.intermediary.com/realtime/step3.aspx

Web Browser Menu Bar

| Patient: Test Patient<br>Date of Service:<br>YYYY-MM-DD | Instructions: All questions associated with each diagnosis in the left column must be appropriately answered to the eligible for higher payment on this claim. A "no" response will require a listed or typed explanation. Refer to "No" options under each question. Only the primary diagnosis requires your response, however you can prescribe additional information therapy to your patient by clicking on other listed guidelines and diagnoses. When completed click the "Done" button. Click "Help" for expanded instructions. |

1.401.1 (P) BENIGN HYPERTENSION
Hypertension

Print Guideline

Hypertension Decision Tree

Are you following this guideline for this patient?

☒ Yes

☒ No

Click here for "no" options

Hypertensive Crisis?

No

If not Hypertensive Crisis Begin Lifestyle Modification: Lose weight, limit alcohol, increase activity, reduce sodium, maintain potassium, calcium, and magnesium, stop smoking, reduce saturated fat, and cholesterol.

Do you wish to prescribe information therapy to this patient?

☒ Yes

☒ No

Click here for "no" options

Not at Goal BP

Initial Drug Choices

Specific Indications

Uncomplicated

Diuretics
Beta-Blockers

Please rate your patient's compliance for this diagnosis.

☒ Complaint

☒ Compliance is a non-factor

☒ No Response

ACE inhibitors Angiotension II Receptor blockers Alpha-blockers Alpha-beta-blockers Beta-blockers calcium antagonists Diuretics

[ Help ]  [ Done ]

Fig. 8A http://www.intermediary.com/realtime/step3.aspx

Web Browser Menu Bar

| Patient: Test Patient<br>Date of Service:<br>YYYY-MM-DD | Instructions: All questions associated with each diagnosis in the left column must be appropriately answered to the eligible for higher payment on this claim. A "no" response will require a listed or typed explanation. Refer to "No" options under each question. Only the primary diagnosis requires your response, however you can prescribe additional information therapy to your patient by clicking on other listed guidelines and diagnoses. When completed click the "Done" button. Click "Help" for expanded instructions. |

2.401.1 (P) BENIGN HYPERTENSION
Hypertension

Are you following this guideline for this patient?
- ☒ Yes
- ☒ No

Click here for options

Do you wish prescribe information therapy patient?
- ☒ Yes
- ☒ No

Click here for "no" options

Please rate your patient's compliance for this diagnosis.
- ☒ Complaint
- ☒ Compliance is a non-factor
- ☒ No Response

[Help] [Done]

Print Guideline

Hypertension Decision Tree

Hypertensive Crisis?

Close
- Co-morbidity
- Emergent Condition
- Pending Lab or other test Result
- Contraindicated because:
- Patient declines for financial reasons
- Patient declines for other reasons:

Begin Lifestyle
alcohol, increase
potassium calcium
reduce saturated fat

Initial Drug Choices

Specific Indications    Uncomplicated

Diuretics
Beta-Blockers

ACE inhibitors Angiotension II Receptor blockers Alpha-blockers Alpha-beta-blockers Beta-blockers calcium antagonists Diuretics

Fig. 9A https://www.intermediary.com

Web Browser Menu Bar

Patient: John Doe    Date of Service:    Physician: Doright

[Instructions]  [Back to Step]

You are reviewing Diagnosis: 401 Essential Hypertension

Please review the evidence-base treatment guideline below and answer the following question:

Are you following this guideline for this patient?
(Note: A "yes" or "no" response are both acceptable. A "no" will prompt a menu of reasons.)

○ Yes
● No

You must select one of the reasons below that will be shared with your patient.
- Co-morbidity
- Emergent condition
- Pending lab or other test results
- Contraindicated because:
- Patient declines for financial reasons;
- Patient declines for other reasons;
- Guideline is in error or out of date;
- Using an advanced treatment with the patient's consent;

[Click here to continue to the next step]

Show Decision Tree: Hypertension

| Evidence-based Medicine Clinical Guidelines | Intermediary Logo |

Hypertension Crisis?

↓ No

- Supporting Inf Is Available
- A Sub-tree is available
- Link to another Resource

FIG. 9B

```
https://www.intermediary.com
```
Web Browser Menu Bar

Patient: John Doe    Date of Service:    Physician: Doright

[Instructions] [Back to Step 3]

You are reviewing Diagnosis: 401 Essential Hypertension

This is the information therapy prescription page. The medical content articles you select on this page will be sent to your patient. Please select content from one or more of the following choices: (Note: You must click "open" to make a selection from the choices below.)

* I want to review and select articles related to this diagnosis (Close)

You may prescribe one or more of the following articles

| Check | | Title | Article ID |
|---|---|---|---|
| ☐ | Preview | Home Blood Pressure Test | Hw227495 |
| ☐ | Preview | Diuretics for high blood pressure | Hw58715 |
| ☐ | Preview | Physical exam for high blood pressure | Hw58824 |
| ☐ | Preview | Beta-blockers for high blood pressure | Hw58939 |
| ☐ | Preview | Angiotensin-converting enzyme (ACE) inhibitors | Hw59141 |
| ☐ | Preview | Calcium channel blockers for high blood pressure | Hw59271 |
| ☐ | Preview | Vasodilators for high blood pressure | Hw59622 |
| ☐ | Preview | High blood pressure (Hypertension) | Hw62787 |

1 2 3 4 5 6 7

[Prescribed Checked Articles]   [Add Checked to my Favorites]   [Preform an Alpha Search]

* I want to view my favorite articles for this diagnosis (open)
* I want to view articles previously prescribed to this patient (open)
* I do NOT want to prescribe information therapy to this patient (open)

FIG. 9C

1st Diagnosis – Web Browser Information Bar

Review medical information related to this diagnosis and answer the questions at the bottom of each section.

*High Blood Pressure – Description*

WHAT IS HYPERTENSION?

Hypertension or high blood pressure is a serious disease that affects nearly 50 million Americans. It causes stroke, heart attack, heart failure, kidney failure, and premature death and disability. It can also cause damage to the eyes and blood vessels. The best way to find high blood pressure is to measure the pressure in the left or right arm. Measuring the blood pressure is important. Once the disease is found, it can be treated with drugs or lifestyle changes.

Blood pressure is simply the pressure within the blood vessels associated with each heartbeat.

401.9/Hypertension NOS

Key Points
Description
Causes
Symptoms
Diagnosis
Prevention & Treatment
Alternative Therapy
Prognosis

Fig. 11 ePPO Claim Wizard Final Questionnaire -- Web Browser Information Bar

Please complete the Following Final Questionnaire (page 1)

1. Did your doctor direct you to this website and discuss the reasons why you should view this information?
   O Yes  O No 2. Did you doctor prescribe medication to you?
   O Yes  O No 3. Are you taking your medications?
   O Yes  O No 4. How are you tolerating your medications?
   O Not Well at All  O Not Very Well  O Well  O Very Well

Fig. 12A http://www.interdmediary.com

Web Browser Menu Bar

Please complete the following...

Are you following the health recommendations?

1. Please share with your doctor how closely you are following the health recommendations as you understand them:
    - Closely Following
    - Mostly Following
    - Somewhat Following
    - Mostly Not Following
    - Not Following

[ Next ]

FIG. 13 https://www.intermediary.com

Web Browser Menu

Please complete the following...

Sharing your responses with your doctor...

In order for you to earn a reward you must agree to make your questionnaire responses (excluding physician ratings) and Program score available to your physician.

I authorize the release of my questionnaire responses and Program score to my physician.

[ I Agree ]  [ I Disagree ]

FIG. 14

```
https://www.intermediary.com
```

Web Browser Menu

Please Complete the Following Final Questionnaire(s)

Rating Your Doctor

1. Did your doctor discuss the benefits of Information Therapy (Ix) with you?

○ Yes
    ○ No

2. Rate your doctor's performance based on what you have read and your understanding of recommended care.

○ Consistent with recommended care
    ○ Mostly consistent with recommended care
    ○ Somewhat consistent with recommended care
    ○ Mostly Inconsistent with recommended care
    ○ Inconsistent with recommended care 3. Do you think your doctor is treating you correctly?

○ Yes
    ○ No

FIG. 15 http://demo.eppopatent.com — Reward Page — Web Browser Information Bar

Confirmation Document        Print / Close

Test Company

Date

Intermediary Participation Confirmation

Congratulations on completing the information therapy process. Your active participation in the Intermediary Program has earned you a financial reward. Your employer / payer has been notified of your participation and you should receive your financial reward by mail in the near future. You may print this document for your records.

Fig. 16

METHODS FOR IMPROVING THE CLINICAL OUTCOME OF PATIENT CARE AND FOR REDUCING OVERALL HEALTH CARE COSTS

CROSS REFERENCE TO RELATED APPLICATION

This application is a continuation of U.S. patent application Ser. No. 13/492,441, filed Jun. 8, 2012, now U.S. Pat. No. 9,171,285, which is a continuation-in-part of U.S. patent application Ser. No. 13/166,467, filed Jun. 22, 2011, which is a continuation of U.S. patent application Ser. No. 11/596,305, filed Dec. 13, 2007, which is a 371 of PCT/US2005/015791 filed May 6, 2005, which is a continuation-in-part of U.S. patent application Ser. No. 10/841,240, filed May 6, 2004, the contents of which are incorporated herein by reference.

BACKGROUND OF THE INVENTION

A challenge confronting modern civilization is how to provide healthcare to all the members of a society. When stated in this way, the challenge transcends the issue of whether healthcare is a right or a privilege. It even exceeds the questions about how much healthcare and what quality of healthcare is a society to receive. Moreover, the challenge is a matter of economic reality—how can society afford universal healthcare coverage. When all is said and done, and there has been lots said and done with regard to this challenge, there are only a handful of consistencies that define the challenge and it is these consistencies that lead us to the solution, The following are the consistencies that frame the challenge:
  Health Status of the Citizens Obviously, a society with a population of healthy versus unhealthy people is better able to provide universal healthcare coverage.
  Efficiency and Effectiveness of the Healthcare Delivery System A society with a healthcare system that delivers high quality clinical outcomes for the least amount of resources is better able to provide universal healthcare coverage than a society with a healthcare system that is dysfunctional and delivers low quality clinical outcomes,
  Affluence of the Society Rich countries are better able to provide universal coverage to its citizens than poor countries. In fact, a country's affluence depends in large part on the health status of its citizens.
  Simply stated, a rich country with healthy people and an efficient healthcare delivery system is in a much better position to provide universal healthcare coverage than a poor country with unhealthy people and a dysfunctional healthcare system. It follows that a society increases its ability to provide universal coverage by improving its economy, its citizen's health status and its healthcare delivery system. So, the challenge can be distilled further to the objective of improving a society's economy, public health status and healthcare delivery system, and then maintaining these factors at levels that allow the society to afford universal healthcare coverage.
  The United States presents an interesting combination of factors that complicate the challenge. The U.S. is an affluent country with declining public health, a largely dysfunctional healthcare delivery system, and since 2008, a struggling economy. Americans spend considerably more on healthcare per capita than citizens of any other developed country, and yet Americans' life expectancy and infant mortality rates rank toward the bottom of the list of these countries. For decades, the growth rate of healthcare expenditures in the U.S. has grown two to five times the rate the economy at large, consuming an ever increasing segment of the country's gross domestic production (GDP). Unlike other developed countries that provide government-sponsored universal healthcare coverage, the U.S. is the only country in which a majority of citizens receive healthcare coverage through their employers or by purchasing health insurance from a commercial insurer. Beginning in the 1990s and continuing to the present, the number of Americans without health insurance coverage or are under-insured has grown because it is becoming increasingly unaffordable. Current estimates place the number of uninsured at 45,000,000 to 47,000,000, which represents an all-time high of 17.1% of the U.S. population as of 2011. At the same time, the annual cost of healthcare coverage for a family of four exceeded. $20,000 for the first time as of 2012.

Fueling this growth in healthcare costs and the uninsured is the declining healthcare status of Americans. The U.S. is far and away the most obese country on earth. According to the Center of Disease Control and Prevention (CDC) latest survey for 2010, 35.7% of American adults are obese. This compares with less than 15% in 1980, 24.2% for the next most obese country (Mexico), and 14.1% for all developed countries. Obesity is a well-known cause of all sorts of serious maladies that are expensive to treat such as diabetes, heart disease, hypertension, and metabolic disease. It is also a well-known fact that obesity can be prevented with better diet and exercise. Studies clearly show that preventing and reversing obesity along with other preventable health issues such as smoking, poor medication adherence and health illiteracy at a moderate level could save enough overall to provide finds to cover all the uninsured and then some.

Complicating matters is the fact that the supply of U.S. physicians to treat these diseases is also becoming an increasingly critical problem. The number of people tilling medical school slots has not kept pace with the demand, especially for primary care physicians. Currently, the United States ranks $43^{rd}$ in the world in the number of physicians per capita and this shortage of physicians is occurring just as the "baby-boomer" generation begins to reach retirement age. The simple economic law of supply and demand will only add inflationary pressure on an already hyper-inflating situation.

Since the mid-1980s, several attempts have been made to control healthcare costs. The attempted reforms only temporarily slowed the escalation of healthcare costs during the mid to late 1990s, when health maintenance organizations (HMOs) incented medical service providers to control healthcare utilization. Successful lawsuits by patients that found HMOs rationed care and the threat of federal legislation (Patients' Bill of Rights) caused a dramatic decline in HMOs. Other approaches in which health plan sponsors (health insurance companies, self-insured employers or government programs) compensate medical service providers (principally physicians) to improve the quality and efficiency of healthcare quality in an attempt to bend the so-called cost curve include:
  the pay-for-performance movement—a concept that assumed improved care quality would lead to cost containment;
  accountable care organizations (ACOs)—a concept that essentially mirrors HMOs with a focus on improved quality to prevent the suggestion of rationed care;

patient-centered medical homes (PCHMs)—a concept that uses primary care providers and health information technology to coordinate better care;

the adoption of interconnected electronic health record (EHR) systems to help make healthcare more effective and efficient.

Again, the reoccurring theme with each of these approaches involves the health plan sponsor compensating medical service providers to change their practice patterns in an attempt to bend the cost curve. The other characteristic common to these approaches is that patients (plan members) are not held accountable for their health behaviors, and therefore, are left out of the equation.

Another movement attempting to resolve the issue of healthcare coverage affordability involves approaches in which the plan sponsor financially rewards the patient to improve his/her health behaviors. Examples of this approach include: wellness, prevention and care management programs the patient (plan member) earns financial rewards for participating in these programs and/or for achieving specific health objectives;

high deductible consumer-driven health care plans this approach includes health savings and retirement accounts that are intended to shift the financial responsibility for purchasing healthcare services to the plan member, thus incenting the plan member to be healthier and a discriminating healthcare shopper;

disease management the plan sponsor hires nurses or coaches to encourage patients with chronic conditions to be compliant with recommended treatments;

population health management to disease management, but includes other methods such as risk assessments, predictive modeling, wellness and prevention to address the complete population, not just chronically ill patients; value-base benefit design (VBBD) or value-based insurance design (VBID)—designed to lower the financial barriers to patients with chronic conditions or use other financial incentives to encourage patient compliance.

In addition to the plan sponsor financially rewarding plan members for participation in these programs or for accomplishing health objectives, the other characteristic common to these approaches is that medical service providers are excluded from the arrangement or have only a perfunctory role.

In essence, there have been two movements attempting to meet the challenge making universal healthcare coverage affordable one in which plan sponsors financially incent medical service providers (service providers and healthcare service providers) to change their practice performance to the exclusion of the patient, and another in which the plan sponsor financial incents patients to improve their health behaviors to the exclusion of the medical service provider. After decades of effort and countless attempts, neither of these movements has succeeded in meeting the challenge.

In 2010, the federal government passed the Patient Protection and Affordable Care Act (PPACA or ACA) for the principal purpose of reducing the number of uninsured Americans. A secondary purpose of the law is to make healthcare less expensive to the country can afford to provide universal coverage. The PPACA's affordability provisions are primarily focused on improving the efficiency and effectiveness of the country's healthcare delivery system. Essentially nothing in the law addresses how to incent Americans to improve their health habits to prevent and reverse preventable conditions such as obesity. As a result, most experts agree that the law cannot effectively resolve healthcare affordability. Therefore, the goal of universal coverage cannot be attained or sustained without either further crippling the U.S. economy or by rationing care to Americans.

So back to the challenge, how can a society such as the U.S. provide healthcare cover to its entire population when the country can't effectively afford the cost of the current system with 17% of its people uninsured? How can people be attracted to the medical profession to alleviate the growing provider supply and demand issue when the economic outlook for the profession seems so gloomy?

The current invention is directed to improving the delivery of healthcare and health behaviors by creating a system of incentives that align the interests of healthcare's essential stakeholders healthcare service providers (principally physicians), healthcare consumers/patients (health plan members), and health plan sponsors (health insurers, self-insured employers, health plans, and the government's Medicare and Medicaid programs) in a win-win-win arrangement. Unlike other cost containment methods that have consistently failed to recognize or accommodate for this fundamental success criterion of stakeholder alignment, the present invention provides an effective system to controlling healthcare costs by "triangulating" the interests of the service provider, the patient and the plan sponsor to improve the standard of care and encourage healthy behaviors, which leads to better health.

The present invention is directed to a method and information technology based system for simultaneously controlling cost by improving the delivery of healthcare related services by medical service providers and improving the health behaviors and status of patients (health plan members) by directing health plan sponsored financial rewards to both the healthcare service provider and the patient for enhancing communication and co-decision-making between medical service providers and patients, increasing the knowledge of the patient about how to self-manage his or her health, providing a system of "checks and balances" to measure and motivate patient and medical service provider adherence to accepted performance standards. As used herein the term "information technology based" means telephonic. Internet, web-based, or other computer based system for recording, storing, processing and communicating information.

SUMMARY OF THE INVENTION

The present invention is directed to a method for improving the delivery of healthcare services and the promotion of healthy behaviors, simultaneous. The method comprises receiving a diagnosed health condition of a patient and a claim for services rendered from a service provider. A service provider performance standard is sent to the service provider based on the received diagnosed health condition. The service provider is queried to generate a service provider declaration of adherence or a reason for non-adherence to the service provider performance standard and a service provider agreement to allow or an acknowledgment that the patient to confirm or rate the service provider declaration of adherence or reason for non-adherence. The diagnosed health condition, the service provider performance standard, the service provider declaration of adherence or the reason for non-adherence, and a patient performance standard are transmitted to the patient. The patient is queried to generate a patient demonstration of knowledge of the diagnosed health condition, a patient declaration of adherence or reason for non-adherence to a patient performance standard, and a patient agreement to allow the service provider to confirm or acknowledge the patient demonstration of knowledge and the patient declaration of adherence or reason for non-adherence to the patient performance standard. The patient demonstration of knowledge, the declaration of patient adherence or reason for non-adherence to the patient performance standard are transmitted or made available to the service provider. The service provider is queried to generate a service provider confirmation of the patient demonstration of knowledge and the declaration of patient adherence or the reason for non-adherence to the patient performance standard. The patient is queried to generate a patient confirmation of the service provider declaration of adherence or reason for non-adherence to the service provider performance standard. The service provider confirmation, the patient confirmation, the service provider declaration of adherence or reason for non-adherence, and the patient demonstration of knowledge, patient declaration of adherence or reason for non-adherence are authenticated and payment of the claim for services rendered and disbursement of a performance-based incentive to the service provider and a performance-based incentive to the service provider are authorized based on authentication.

The present invention is further directed to an information technology based, such as a web-based or telephonic method, for managing healthcare delivery and for promoting healthy behavior. The method comprises receiving a patient identification and at least one diagnosis from a service provider through a web or telephonic interface. The method further includes transmitting a service provider performance standard, a patient performance standard and patient educational articles to the service provider corresponding with each diagnosis received from the service provider through the web or telephonic interface. A service provider declaration of adherence to the service provider performance standard or a reason for non-adherence is received from the service provider. An information therapy prescription of one or more patient educational articles, a prescription of the patient performance standard, and a rating of patient adherence to a patient performance standard are received from the service provider. Authorization from the service provider to allow the patient to verify or rate the service provider declaration of adherence to the performance standard or to express an opinion about the reason for non-adherence, and to have the service provider declaration of adherence to the service provider performance standard or the reason for non-adherence that authenticated and adjudicated. Disbursement of a performance-based incentive to the service provider based upon verification by the patient and authentication and adjudication of the service provider declaration of adherence or the reason for non-adherence to the performance dr d is occurs upon receipt of verification by patient.

The present invention further includes a system for managing healthcare delivery and for promoting healthy behaviors. The system comprises a healthcare services provider web-based or telephonic interface, a patient web-based or telephonic interface, and a means to automatically authenticating and adjudicating. The healthcare services provider web-based or telephonic interface is adapted to accept a patient identification and a diagnosis from a healthcare services provider, to transmit a healthcare service provider performance standard, a healthcare service provider agreement to allow the patient to confirm or rate the healthcare service provider declaration of adherence or the healthcare provider reason for non-adherence to the healthcare provider performance standard, a patient performance standard, and patient educational articles to the healthcare services provider based upon the diagnosis, to accept a healthcare service provider declaration of adherence or reason for non-adherence to the healthcare service provider performance standard, optionally to accept an after-the-fact healthcare service provider rating of patient adherence to the patient performance standard, to accept a healthcare service provider information therapy prescription of one or more of the patient educational articles to the patient, and to accept healthcare service provider verification of a patient declaration of adherence to the patient performance standard. The patient web-based or telephonic interface is adapted to provide the patient with the healthcare service provider performance standard, the patient performance standard, the information therapy prescription, and a patient agreement to allow the service provider to confirm or rate a patient declaration of adherence or reason for non-adherence to the patient performance standard and a patient answer to a query regarding the information therapy prescription, to provide at least one query to the patient regarding the information therapy and the patient performance toward, to receive at least one answer to the at least one query regarding the information therapy and the agreement to allow the service provider to confirm or rate the patient declaration of adherence or reason for non-adherence to the patient performance standard and the patient answer to the query regard the information therapy prescription, to accept the patient declaration of adherence or reason for non-adherence to the patient performance standard, to accept the patient agreement answer to allow the service provider to confirm or rate the patient declaration of adherence or reason for non-adherence to the patient performance standard and the patient answer to the query regard the information therapy prescription, to accept a patient verification of the service provider declaration of adherence or reason for non-adherence to the service provider performance standard. The means for automatically adjudicating and authenticating the service provider declaration of adherence, the patient declaration of adherence, the service provider agreement to allow the patient to confirm or rate the service provider, the patient agreement to allow the service provider to confirm or rate the patient, the patient verification of the healthcare service provider declaration of adherence, and the healthcare service provider verification of the patient declaration of adherence; for providing an authorization for disbursement of a performance-based reward to the patient and a performance-based reward to the services provides upon adjudication and authentication.

BRIEF DESCRIPTION OF THE FIGURES.

FIGS. 2 and 2A are a flow chart representing the patient's portion of one embodiment of the Program.

FIG. 5 is an illustrative representation of a webpage used in the method of the present invention. The webpage shown represents a step in the method of accepting a patient's member ID or last name.

FIG. 6 is a representative webpage interface used to accept a diagnosis from a service provider, FIG. 7 is an illustrative webpage interface that may be used in the present invention. The webpage of FIG. 7 is adapted to accept multiple diagnoses from a service provider, if necessary.

FIG. 8A is a webpage interface designed to guide the service provider through the performance-based standards for a selected diagnosis.

FIG. 9A is an exemplary webpage of the present invention illustrating the interactive nature of the present invention by showing a menu of reasons for non-adherence upon deviation from the performance standard.

FIG. 9B is an alternative exemplary webpage of the present invention illustrating the interactive nature of the present invention by showing a menu of reasons for service provider non-adherence upon deviation from the performance standard.

FIG. 9C is an exemplary information therapy prescription webpage.

FIG. 12A illustrates an exemplary webpage comprising a questionnaire used to allow the patient to indicate his/her knowledge or understanding of the health information provided by the webpage shown in FIG. 11.

FIG. 13 is an exemplary webpage showing an inquiry of the patient to share the patient's opinion as to how closely he or she is following health recommendations.

FIG. 14 is an exemplary webpage used to allow the patient to authorize release of the patient's responses to an information therapy questionnaire to the patient's service provider.

FIG. 15 is an exemplary webpage used by the patient to rate his or her service provider.

FIG. 16 is an exemplary voucher used to notify the patient they have completed the information therapy process and earned a financial reward.

DESCRIPTION OF THE PREFERRED EMBODIMENTS

Figure 1:
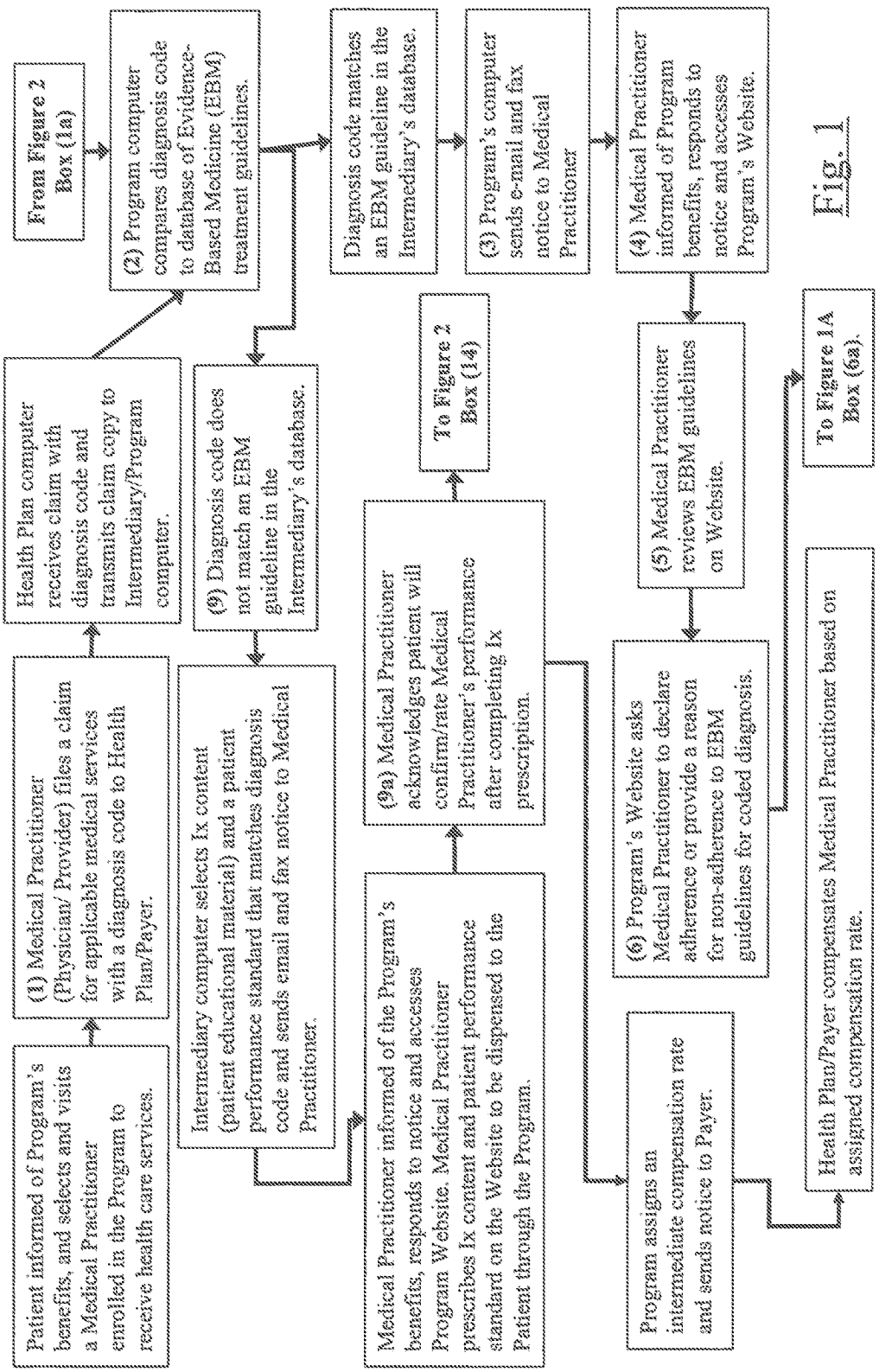
FIGS. 1 and 1A are a flow chart representing the medical practitioner's (service provider's) portion of one embodiment of the Program.

The current invention is often referred to as a healthcare "pay-for-perthrmance" or "P4P" program. Most P4P programs exclusively reward or motivate medical providers (doctors and hospitals). The current invention rewards both the medical provider and the patient "interactively" in a manner that creates a simultaneous benefit to the service provider, the patient, and the purchaser/payer (health plan). The current invention may preferably be described as an "alignment of interest" or "AOI" program because it aligns the interest of the medical provider, the patient and the health plan sponsor in a "win-win-win arrangement.

The current invention typically involves four (4) parties: the medical service provider or practitioner (doctors); the patient (consumer or health plan member); the party who underwrites the cost or risk of the healthcare (purchaser or payer or employer or insurer or government or health plan or health plan sponsor); and the independent operator of the invention (referred to as an intermediary or "Informediary")

The current invention also comprises the following elements: a performance standard (or set of performance standards) for both the medical provider and the patient that have been shown (preferably by an independent and credible third party) to be effective at improving healthcare and health in a manner that controls healthcare costs; performance-based incentives that may comprise financial rewards paid by the health plan to the medical provider and patient; a web-based or telephonic system of checks and balances that asks the medical provider and the patient to independently and individually declare adherence or provide a reason for non-adherence to the respective performance standard, asks the medical provider and the patient to independently and individually agree to allow the other party to confirm his/her declaration of adherence or reason for non-adherence, and further asks the service provider and patient to independently and individually confirm each other's declaration of adherence or reason for non-adherence; and a website (Website) operated by the Informediary that comprises a set of proprietary Internet applications that facilitates the system of checks and balances.

In the current invention, the health plan disburses performance-based financial rewards independently to the medical provider and patient when the Informediary authenticates that the medical provider and/or the patient have accessed the Website, demonstrated or gained. knowledge about the respective performance standards, declared adherence or provided a reason for non-adherence to the performance standards, agreed to allow the other party to confirm his/her declaration of adherence or reason for non-adherence, and confirmed (or denied) the adherence to the performance standard by the other party.

The current invention is designed to "bolt on" to health plans (including plans sponsored by health insurers, the government's Medicare and Medicaid programs, and self-insured employers) to improve health and healthcare in a manner that leads to healthcare cost containment. In some respects, the current invention creates a platform by which a three-way contract or partnership can be established between the health plan, healthcare service providers and patients, which is administered by the intermediary. Accordingly, health plans are potential customers of the current invention, while healthcare service providers and patients are users. Other terms used to describe the result achieved by the current invention include: "triangulation" and "triangulation to reach a state of equilibrium;" "mutual accountability," "mutual accountability partnership," and "doctor-patient mutual accountability."

The Information Therapy (Ix) Program provided by the current invention directs the health plan to financially reward healthcare service providers medical practitioners) and patients "interactively" for controlling healthcare costs and utilization through the incorporation of evidence-based medicine treatment guidelines, information therapy, best clinical practices, and healthy behaviors, which are collectively referred to as performance standards of the Ix Program. The current invention is delivered through a proprietary Internet Website where doctors (medical practitioners) and patients read pertinent medical content and respond to a series of questions to determine, declare, acknowledge, confirm, and motivate compliance to performance standards that have been shown to improve the standard of care and the level of health, which in turn, lead to lower healthcare costs. The invention is intended to compliment other quality improvement and cost containment methods and initiatives such as: disease management; consumer-driven healthcare; accountable care organizations (ACOs); patient centered medical homes (PCMHs); population health management including health risk assessment, readiness to change, health screenings, wellness examinations, wellness and fitness programs, smoking cessation, predictive modeling; medical malpractice risk management; the adoption of personal health records (PHRs), recommended hospital care management programs; pre-authorization certification of expensive procedures and tests; pharmacy benefit management including electronic prescribing, therapeutic substitutions, and drug interaction; electronic health monitoring devices; and the adoption of electronic health (medical) record (EHR) systems and the related meaningful use criteria.

Rewarding medical practitioners (physicians and hospitals) in this fashion is commonly referred to as "pay-for-performance" or "P4P." It is also referred to as "value-based" healthcare, in contrast to "volume-based" healthcare. However, the current invention's incentive system is unlike any other P4P program in that financial rewards are paid by the health plan (healthcare purchaser/payer) to both the medical provider (practitioner) and the patient for voluntarily, individually and independently (or dependently) declaring (or demonstrating) compliance to performance standards (that are known to improve health and healthcare that leads to reduced utilization and cost of healthcare services) through the invention's Website, and also for agreeing to allow the other party to individually and independently confirm (verify or acknowledge) each other's (his/her) declaration (or demonstration) of adherence to performance standards through the Website. In effect, the current invention directs health plan sponsored financial rewards to both medical practitioners and patients to invoke powerful psychosocial motivators inherent to the doctor-patient relationship by asking the medical practitioner and the patient to voluntarily serve as each other's "judge and jury" as to the other person's adherence to performance standards known to improve health and healthcare. The innate desire by both the medical practitioner and patient to please one another augments the financial incentives to increase adherence to the performance. Since the invention is accomplished through a proprietary Internet Website that allows for an independent third party or a health plan to authenticate and report the medical practitioner and patient's "declarations and confirmations", a natural check and balance (mutual accountability) is created that serves as a very effective and efficient means (incentive) to shape the behaviors of the medical practitioner (provider) and the patient, which again, is above and beyond the invention's financial rewards. This process of "declare and confirm" and "demonstrate and acknowledge" create "checks and balances" that defines the terms "doctor-patient mutual accountability" and "interactive" rewards and incentives. In the present invention, the interests of the medical practitioner (provider), the patient and the health plan (purchaser/payer) are aligned in a "win-win-win" arrangement that define the terms "triangulation to reach a state of equilibrium" and "mutual accountability partnership."

More specifically, medical practitioners "win" by being compensated for rendering a higher standard of care, by earning the admiration of their patients, by enhancing their reputation and image with their peers, and by the personal satisfaction of providing superior care to their patients. Patients "win" by earning financial rewards for demonstrating knowledge of and compliance to healthy behaviors and rating their medical practitioner's performance; by gaining knowledge, empowerment and motivation to self-manage their health; by attaining the peace of mind that their medical practitioners are rendering recommended EBM care; and by achieving the satisfaction that their doctor is aware of their health literacy and adherence to the performance standard. Health plans "win" by gaining a means to better insure that they are receiving greater value for their healthcare purchases, plus a means to adjust both the size and nature of the rewards and performance standards to improve healthcare and healthiness to achieve cost savings that produce a return on investment. Because of its unique aligning feature, the invention could be described as an "alignment of interest" or "AOI" program as opposed to a P4P program.

The current invention provides an $I_x$ (Ix) Program model that rewards service providers (medical practitioners) financially and in other ways when they adhere or provide a reason for non-adherence to a performance standard such as considering an EBM treatment guidelines, prescribing $I_x$ to their patients, and agreeing to allow their patients to confirm or rate their adherence or reason for non-adherence to the performance standard through a medical practitioner Internet Website application. The rewards, however, may comprise financial rewards or other rewards limited in their type and nature by the imagination of the health plan customer of the current invention. The same holds true for performance standards. In addition to EBM treatment guidelines and Ix prescriptions, a medical practitioner performance standard could also be any service that is independently judged and validated to be beneficial to the patient that can be structured interactively through the invention's Website. Examples of these types of performance standards include: patient-integrated pre-authorization certification of expensive medical services; patient-integrated hospital care management systems; drug therapy (pharmacy benefit) management programs including e-prescription, therapeutic drug substitution, automated drug interactions, and patient pharmacy education with knowledge verification; the adoption and use of personal health records; medical education programs; wellness and fitness programs; social networking therapy programs; health risk assessments; readiness to change interventions; compliance to recommended treatments; use of automatic health monitoring devices; hospitalization pre-admit and discharge education and adherence programs; provider quality and cost education and transparency; and adoption of health self-management programs. In effect, the health plan can choose a specific health objective, such as prenatal care with self-management testing that is confirmed by a licensed obstetrician (who is compensated for the extra time and liability). Then the health plan can specify an extra amount of financial rewards, such as $200 for patient adherence against this performance standard, whereas a normal patient financial reward may be $25. The health plan's objective is to prevent health problems for the mother and child, and the associated costs by using both a financial reward and the psychosocial motivators inherent to the doctor-patient relationship. This process illustrates just one of countless ways a health plan can use the invention to target a specific health or cost objective, it is referred to a "precision-guided rewards and performance standards."

In the Ix program model of the current invention, the process of a service provider, such as a medical practitioner, physician, doctor, clinician, chiropractor, nurse, dentist, or other health care service provider, accessing the Website to "practice the method" (Ix Program or Program) by considering EBM, prescribing Ix, and agreeing to allow the patient to confirm/rate the doctor's performance can be initiated as a result of the doctor's normal insurance claim tiling. The receipt of a claim for an applicable service, such as a patient office visit, prompts the independent intermediary to send an email or fax notification to the doctor. This "after-the-fact" notification directs the doctor to access the Website to "practice the Program," In this example, when the doctor successfully responds to the Website, the independent intermediary notifies the health plan to compensate the doctor for practicing the Program for the associated patient office visit. This implies that the method facilitates timely and direct physician (service provider) compensation for each patient encounter on a per-occurrence-of-care basis. This method of compensation is considered "Pavlovian" in that physicians receive quick rewards that are directly tied to their performance. Other incentive-based (P4P) programs that compensate physicians in an indirect and untimely fashion, such as annual payments, are often based on formulas designed to measure a variety of performance criteria and judged by a third party. Physicians find these types of incentive-based programs objectionable, especially when compensation is based on complicated formulas or dependent on patient performance or involve "cookbook medicine" or judge by third parties that physicians do not trust.

In a preferred embodiment of the current invention, doctors can initiate the process during the patient office visit on a "real-time" basis through the medical practitioner (service provider) Internet Website application. The doctor's appropriate responses entered into the Website affect an immediate information therapy prescription to the patient. The doctor's responses are stored in the independent intermediary's Website database. When the doctor files an insurance claim for an applicable medical practitioner service (such as a patient office visit), the claim is forwarded (typically through the health plan's administrator by electronic means) to the independent intermediary. The claim is then linked to the doctor's stored Website responses. The independent intermediary then notifies the health plan to compensate the doctor for practicing the program for the associated patient office visit.

As described earlier, the current invention can also be initiated "after-that-fact" when the independent intermediary identifies applicable medical practitioner services from the tiling of a claim for reimbursement. This triggers an e-mail notification from the independent intermediary to the medical practitioner (doctor). The doctor responds to the e-mail through the medical practitioner Website. The medical practitioners appropriate responses can affect an automatic payment or reimbursement increase to the medical practitioner (for practicing the Program and an information therapy prescription to the patient.

When the patient receives the Ix prescription by mail or e-mail (or handed to the patient during the encounter by the doctor), he/she is directed to a patient Website. There the patient is asked to read evidence-based medical content and answer a series of questions. These questions are designed to test the patients understanding of his/her condition, the recommended treatments and healthy behaviors, and how best to self-manage his/her condition. These questions also determine the patient's adherence or reason for non-adherence to recommended treatment, agreement to allow his/her doctor to confirm/acknowledge/rate his/her adherence or reason for non-adherence to the recommended treatments and healthy behaviors, and seek his/her impression of the doctor's care relative to recommended care (treatments). As the patient answers these questions, the patient scores points toward a financial reward or refund of the patient's out-of-pocket medical expenses. The patient's score and corresponding reward amount is automatically transmitted by the independent intermediary to the patient's health plan, which makes the disbursement of a performance-based reward to the patient. As used herein, "independent intermediary" may also include the patient's health plan. In an alternative embodiment of this model of the invention, the independent intermediary can disburse the performance-based rewards to doctors and patients from funds supplied by the health plan. The current invention provides for the automatic or optional forwarding of the patient's actual responses by the independent intermediary through the Website to the patient's doctor to support subsequent care and as a means for the doctor to confirm/acknowledge the patients declaration or demonstration of adherence to a performance standard. Alternatively, the intermediary can post the patient's responses on a secured section of the Website for the doctor to access for follow-up and confirmation purposes.

The current invention has a number of built-in features that are designed to achieve service provider (doctor) and patient acceptance. One of these features addresses concerns doctors have about being forced to practice "cookbook medicine." The current invention allows and, in fact, encourages service providers (medical practitioners/doctors/physicians/clinicians/healthcare or medical service providers) to deviate from treatment guidelines when it is appropriate in their judgment. The service provider Website offers the doctor a menu of reasons to deviate or the doctor can briefly describe a reason for non-adherence, provided the doctor agrees to allow the patient to review/concur with the reason for deviation/non-adherence. When the doctor provides a reason for deviating from (non-adherence to) a guideline, the intermediary stores that reason in the Website database to be presented to the patient later in the process. When the patient accesses the Website (which is described below), one of the questions he/she is asked to answer is to rate or express an opinion about the doctor's reason for deviating from a guideline. As a result, the health plan is served (wins) by this feature of the current invention because the doctor knows his/her reason for deviation (or for that matter, declaration of guideline adherence) will be rated/confirmed by the patient, which may cause the patient's opinion of the doctor's care to be reinforced—or diminished to the point the patient may refer the doctor to others or seek care elsewhere. Doctors are aware that their patients are gaining valuable information through the Program and doctors know that their patients will expect care that is aligned with evidence-based and/or recommended treatments, Doctors also become aware that they are being rated by their patients against evidenced-based and recommended care. Though this rating may or may not directly impact an individual doctor's compensation on a per-occurrence-of-care basis, most doctors do not want their patients to think/learn they may be practicing inferior medicine, nor do doctors want their aggregate patient rating to cause them to be ranked poorly against their peers or to suffer negative consequences because a poor aggregate rating or a low ranking may be published. This check and balance aspect of the current invention serves as an important incentive to encourage doctors to be adherent to guidelines or to provide appropriate reasons for deviation from a guideline. Doctors are served (win) by this feature of the current invention because this check and balance feature alleviates the concerns medical practitioners (doctors) have about being forced to practice "cookbook medicine" and helps doctors better communicate and educate their patients. Patients are served (win) because the Program communicates their doctor's reason for deviation so patients can understand that a particular guideline does not necessary fit a specific medical condition. This feature also helps the developers of guidelines and medical researchers determine which guidelines are strongest and which ones need further research and development.

Another feature of the current invention provides for the efficient and effective dissemination of advancements in medicine to service providers (medical practitioners) and serves as a means (incentive system) to encourage doctors to adopt new and proven advancements in medicine. This feature accomplishes these objectives by highlighting new advancements in the decision-tree guidelines or medical content presented in the medical practitioner Website. The Website can require the medical practitioner to read the highlighted guideline or content that contains research studies or literature that supports the advancement. The medical practitioner can also be required to answer a questionnaire or indicate an acknowledgement or take a test about the medical advancement in order for the medical practitioner to receive compensation and/or to earn the higher rates of reimbursement offered through the Program. The successful completion of the questionnaire or test may earn the medical practitioner credits toward required continuing medical education (CME). The current invention may also forward (electronically or otherwise) the results of the questionnaire to the medical practitioner's licensure board for accreditation purposes. Since the doctor is already asked to declare adherence or provide a reason for non-adherence to the guideline, adoption of medical advancements can be accelerated.

Though the service provider and patient psychological incentives (psychosocial motivators inherent to the doctor-patient relationship) are interactive in that both parties are aware that they will be asked to judge/acknowledge each other's declaration/demonstration of adherence (or non-adherence) to performance standards against their actual performance (adherence), the current invention ideally (but not necessarily) separates the financial reward provided to the medical practitioner from the reward provided to the patient. Thus, the medical practitioner may be paid for his/her time and effort independent (or dependent) to how the medical practitioner's patients respond to their Ix or adherence (non-adherence) to a patient performance standard. Patients' performance-based rewards may also be independent (or dependent) of the medical practitioners' participation/adherence, prescribing information therapy or adherence to the medical practitioner performance standards. In other words, the reward strategies involving participant elections/Website choices of the current invention have been purposely configured to create a natural and beneficial check and balance between doctors and the patients. This set of strategic checks and balances ("doctor-patient mutual accountability") solves the issues of compliance monitoring and appropriate provider deviation from a guideline that other incentive-based models cannot solve.

The current invention provides a method for delivering healthcare services designed to tower healthcare costs by elevating the standard of care and encouraging patients to lead healthier lives through a web-based/telephonic interface, provider-patient interactive incentive (reward) system. An application of the method comprises the steps of receiving a claim for compensation for medical services from a medical practitioner for medical treatment of a patient covered by the invention's program. The claim includes at least one applicable diagnosis code corresponding to at least one applicable medical treatment (such as an office visit) rendered to patient. If at least one diagnosis code of the submitted claim corresponds to a medical diagnosis found in a database of applicable medical diagnoses, then a notice is sent by the independent intermediary, also known as an Informediary, to the medical practitioner, directing the medical practitioner to voluntarily access a Website operated by an informediary. The Website presents the medical practitioner with EBM treatment guidelines or other pertinent medical content elating to the medical diagnosis of the patient. In addition to rendering the common/recommended medical treatment, the medical practitioner prescribes Ix for said patient that provides the patient with instructions concerning managing the medical condition/diagnosis and living a healthy lifestyle. The medical practitioner may be given the opportunity to rate the patient's compliance with the prescribed information therapy, recommended treatments, and instructions relating to a healthy lifestyle.

In another embodiment, the current invention provides a method for delivering healthcare services through a web-based/telephonic interface, interactive provider-patient incentive (reward) system. One method of the current invention comprises the steps of the Informediary receiving a claim for compensation for medical services rendered by a medical practitioner to a patient covered by the Program of the current invention. The claim filed by the medical practitioner includes at least one applicable diagnosis code corresponding to at least one applicable medical treatment rendered to said patient. Upon receipt by the Informediary, the claim is examined to determine if at least one diagnosis code corresponds to an applicable medical diagnosis found in a database of applicable medical diagnoses. If a corresponding applicable medical diagnosis is present, then a notice is sent by the Informediary to the medical practitioner. The notice sent to the medical practitioner includes the instructions necessary for accessing a medical practitioner Website. Once the medical practitioner gains access to the Website, the medical practitioner will have access to EBM treatment guidelines (if one exists) relating to the medical diagnosis/diagnoses of the patient. Thereafter, the medical practitioner declares/demonstrates adherence or provides a reason for non-adherence to the EBM treatment guideline (if one exists), agrees to allow the patient to confirm/rate the medical practitioner's declaration/demonstration of adherence or reason for non-adherence to the EBM treatment guideline, and then prescribes educational material in the form of information therapy to the patient relating to the medical diagnosis/diagnoses through the Website application. The prescribed information therapy includes instruction for the patient to self-manage his/her medical condition, guidelines for healthy behavior, and a means to assess/determine/test the patient's understanding (health literacy) of the educational material. Additionally and alternatively, the medical practitioner rates patient adherence to the prescribed Ix and recommended treatments and healthy behaviors. Following the prescription of Ix, the Informediary automatically generates a notice to the patient directing the patient to access the Website. Once the patient accesses the Website, the Website provides the patient with the means to access the educational material relating to his/her medical diagnosis/diagnoses. The method further provides for the monitoring of the patient's access of the medical information. The Website further provides a knowledge exam/assessment/test designed to measure patient comprehension of the medical diagnosis, how his/her doctor (medical practitioner) should be treating the diagnosis, and how the patient can/should self-manage his/her condition. Provided that the patient takes the exam or declares his/her understanding, the Website will automatically score the knowledge exam and it will provide the patient with the option of (or require) forwarding (posting for access) the knowledge exam or declaration of understanding results to the medical practitioner. The patient is also asked to indicate their personal adherence or reason for non-adherence to recommended care and healthy behaviors, to report their health status, to agree to allow his/her medical practitioner to confirm/rate/acknowledge the patient's knowledge exam/declaration and declaration/demonstration of adherence (or reason for non-adherence) to recommended care and healthy behaviors, and to rate their medical practitioner's performance against the recommended care. Finally, the patient is provided with the option of authorizing the compliance rating assigned by his/her medical practitioner to the patient's health plan and/or employer for the purpose of determining a financial or other types of reward.

In a further embodiment of the current invention, the patient is provided with the option of rating (or is required to rate) the medical practitioner's adherence or reason for non-adherence to EBM treatment guidelines or other accepted care corresponding to the patient's diagnosis. Following review of the prescribed Ix educational material, the patient is asked to rate the medical practitioner's care against the Ix educational material. This rating ideally does not, though it may, directly affect that medical practitioner's reward or compensation on a case-by-case basis. However, it does begin to build an overall clinical performance rating for that medical practitioner. This can be used to help individual medical practitioners measure their performance against their peers. Poor ratings can be used in peer review. This embodiment of the invention allows and encourages medical practitioners the freedom to use their clinical judgment to deviate from a guideline while receiving the maximum financial reward, provided the medical practitioner selects or supplies a reason for the deviation and agrees to allow the patient to concur with/acknowledge/rate the medical practitioner's reason for non-adherence. Preferably, the ratings provided by the medical practitioner and the patient would be obscured from each other to help protect the doctor-patient relationship with each party having the option of releasing his/her rating to the other party.

Still further, the current invention provides a method for delivering healthcare services through a web-based/telephonic interface, interactive provider-patient incentive (reward) system. The system of the current invention comprises a Website operated by an Informediary and having a medical practitioner portion/section and a patient portion/section. The medical practitioner's portion is programmed to be accessed directly by the medical practitioner during the patient encounter (the "real-time" method) or to receive a claim submitted by the medical practitioner after the patient encounter containing standard codes for the patient's diagnosis(es) and medical services rendered by the medical practitioner (the "after-the-fact" method). The Website compares the medical diagnosis(es) entered by the medical practitioner directly into the Website during the patient encounter or from a coded claim submitted by the medical practitioner to a database of medical diagnoses.

In the Ix program model of the current invention, the process of a service provider accessing the Website to "practice the method" (Ix Program or Program) by considering EBM, prescribing Ix, and agreeing to allow the patient to confirm/rate the service provider's performance can be initiated as a result of the doctor's normal insurance claim filing. The receipt of a claim for an applicable service, such as a patient office visit, prompts the independent intermediary to send an email or fax notification to the doctor. This "after-the-fact" notification directs the doctor to access the Website to "practice the Program." In this example, when the doctor successfully responds to the Website, the independent intermediary notifies the health plan to compensate the doctor for practicing the Program for the associated patient office visit. This implies that the method facilitates timely and direct physician (service provider) compensation for each patient encounter on a per-occurrence-of-care basis. This method of compensation is considered "Pavlovian" in that physicians receive quick rewards that are directly tied to their performance. Other incentive-based (P4P) programs that compensate physicians in an indirect and untimely fashion, such as annual payments, are often based on formulas designed to measure a variety of performance criteria and judged by a third party. Physicians find these types of incentive-based programs objectionable, especially when compensation is based on complicated formulas or dependent on patient performance or involve "cookbook medicine" or judge by third parties that physicians do not trust.

In a preferred embodiment of the current invention, doctors can initiate the process during the patient office visit on a "real-time" basis through the medical practitioner (service provider) Internet Website application. The doctor's appropriate responses entered into the Website affect an immediate information therapy prescription to the patient. The doctor's responses are stored in the independent intermediary's Website database. When the doctor files an insurance claim for an applicable medical practitioner service (such as a patient office visit), the claim is forwarded (typically through the health plan's administrator by electronic means) to the independent intermediary. The claim is then linked to the doctor's stored Website responses. The independent intermediary then notifies the health plan to compensate the doctor for practicing the program for the associated patient office visit As described earlier, the current invention can also be initiated "after-that-fact" when the independent intermediary identifies applicable medical practitioner services from the filing of a claim for reimbursement. This triggers an e-mail notification from the independent intermediary to the medical practitioner (doctor). The doctor responds to the e-mail through the medical practitioner Website. The medical practitioners appropriate responses can affect an automatic payment or reimbursement increase to the medical practitioner for practicing the Program) and an information therapy prescription to the patient.

When the patient receives the Ix prescription by mail or e-mail (or handed to the patient during the encounter by the doctor), he/she is directed to a patient Website. There the patient is asked to read evidence-based medical content and answer a series of questions. These questions are designed to test the patient's understanding of his/her condition, the recommended treatments and healthy behaviors, and how best to self-manage his/her condition. These questions also determine the patient's adherence or reason for non-adherence to recommended treatment, agreement to allow his/her doctor to confirm/acknowledge/rate his/her adherence or reason for non-adherence to the recommended treatments and healthy behaviors, and seek his/her impression of the doctor's care relative to recommended care (treatments). As the patient answers these questions, the patient scores points toward a financial reward or refund of the patient's out-of-pocket medical expenses. The patient's score is automatically forwarded by the independent intermediary to the patient's health plan, which makes the disbursement of a performance-based reward to the patient. In an alternative embodiment of this model of the invention, the independent intermediary can disburse the performance-based rewards to doctors and patients from funds supplied by the health plan.

The current invention provides for the automatic or optional forwarding of the patient's actual responses by the independent intermediary through the Website to the patient's doctor to support subsequent care and as a means for the doctor to confirm/acknowledge the patient's declaration or demonstration of adherence to a performance standard. Alternatively, the intermediary can post the patient's responses on a secured section of the Website for the doctor to access for follow-up and confirmation purposes, The current invention has a number of built-in features that are designed to achieve service provider (doctor) and patient acceptance. One of these features addresses concerns doctors have about being forced to practice "cookbook medicine." The current invention allows and, in fact, encourages service providers (medical practitioners/doctors/physicians/clinicians/healthcare or medical service providers) to deviate from treatment guidelines when it is appropriate in their judgment. The service provider Website offers the doctor a menu of reasons to deviate or the doctor can briefly describe a reason for non-adherence, provided the doctor agrees to allow the patient to review/concur with the reason for deviation/non-adherence. When the doctor provides a reason for deviating from (non-adherence to) a guideline, the intermediary stores that reason in the Website database to be presented to the patient later in the process. When the patient accesses the Website (which is described below), one of the questions he/she is asked to answer is to rate or express an opinion about the doctor's reason for deviating from a guideline. As a result, the health plan is served (wins) by this feature of the current invention because the doctor knows his/her reason for deviation (or for that matter, declaration of guideline adherence) wilt be rated/confirmed by the patient, which may cause the patient's opinion of the doctor's care to be reinforced—or diminished to the point the patient may refer the doctor to others or seek care elsewhere. Doctors are aware that their patients are gaining valuable information through the Program and doctors know that their patients will expect care that is aligned with evidence-based and/or recommended treatments. Doctors also become aware that they are being rated by their patients against evidenced-based and recommended care. Though this rating may or may not directly impact an individual doctor's compensation on aper-occurrence-of-care basis, most doctors do not want their patients to think/team they may be practicing inferior medicine, nor do doctors want their aggregate patient rating to cause them to be ranked poorly against their peers or to suffer negative consequences because a poor aggregate rating or a low ranking may be published. This check and balance aspect of the current invention serves as an important incentive to encourage doctors to be adherent to guidelines or to provide appropriate reasons for deviation from a guideline. Doctors are served (win) by this feature of the current invention because this check and balance feature alleviates the concerns medical practitioners (doctors) have about being forced to practice "cookbook medicine" and helps doctors better communicate and educate their patients. Patients are served (win) because the Program communicates their doctor's reason for deviation so patients can understand that a particular guideline does not necessary fit a specific medical condition. This feature also helps the developers of guidelines and medical researchers determine which guidelines are strongest and which ones need further research and development.

Another feature of the current invention provides for the efficient and effective dissemination of advancements in medicine to service providers (medical practitioners) and serves as a means (incentive system) to encourage doctors to adopt new and proven advancements in medicine. This feature accomplishes these objectives by highlighting new advancements in the decision-tree guidelines or medical content presented in the medical practitioner Website. The Website can require the medical practitioner to read the highlighted guideline or content that contains research studies or literature that supports the advancement. The medical practitioner can also be required to answer a questionnaire or indicate an acknowledgement or take a test about the medical advancement in order for the medical practitioner to receive compensation and/or to earn the higher rates of reimbursement offered through the Program. The successful completion of the questionnaire or test may earn the medical practitioner credits toward required continuing medical education (CME). The current invention may also forward (electronically or otherwise) the results of the questionnaire to the medical practitioner's licensure board for accreditation purposes. Since the doctor is already asked to declare adherence or provide a reason for non-adherence to the guideline, adoption of medical advancements can be accelerated.

Though the service provider and patient psychological incentives (psychosocial motivators inherent to the doctor-patient relationship) are interactive in that both parties are aware that they will be asked to judge/acknowledge each other's declaration/demonstration of adherence (or non-adherence) to performance standards against their actual performance (adherence), the current invention ideally (but not necessarily) separates the financial reward provided to the medical practitioner from the reward provided to the patient. Thus, the medical practitioner may be paid for his/her time and effort independent (or dependent) to how the medical practitioner's patients respond to their Ix or adherence (non-adherence) to a patient performance standard. Patients performance-based rewards may also be independent (or dependent) of the medical practitioners' participation/adherence, prescribing information therapy or adherence to the medical practitioner performance standards. In other words, the reward strategies involving participant elections/Website choices of the current invention have been purposely configured to create a natural and beneficial check and balance between doctors and the patients. This set of strategic checks and balances ("doctor-patient mutual accountability") solves the issues of compliance monitoring and appropriate provider deviation from a guideline that other incentive-based models cannot solve.

The current invention provides a method for delivering healthcare services designed to lower healthcare costs by elevating the standard of care and encouraging patients to lead healthier lives through a web-based/telephonic interface, provider-patienteractive incentive (reward) system. An application of the method comprises the steps of receiving a claim for compensation for medical services from a medical practitioner for medical treatment of a patient covered by the invention's program. The claim includes at least one applicable diagnosis code corresponding to at least one applicable medical treatment (such as an office visit) rendered to patient. If at least one diagnosis code of the submitted claim corresponds to a medical diagnosis found in a database of applicable medical diagnoses, then a notice is sent by the independent intermediary, also known as an Informediary, to the medical practitioner, directing the medical practitioner to voluntarily access a Website operated by an Informediary. The Website presents the medical practitioner with EBM treatment guidelines or other pertinent medical content relating to the medical diagnosis of the patient. In addition to rendering the common/recommended medical treatment, the medical practitioner prescribes Ix for said patient that provides the patient with instructions concerning managing the medical condition/diagnosis and living a healthy lifestyle. The medical practitioner may be given the opportunity to rate the patients compliance with the prescribed information therapy, recommended treatments, and instructions relating to a healthy lifestyle, In another embodiment, the current invention provides a method for delivering healthcare services through a web-based/telephonic interface, interactive provider-patient incentive (reward) system. One method of the current invention comprises the steps of the Informediary receiving a claim for compensation for medical services rendered by a medical practitioner to a patient covered by the Program of the current invention. The claim filed by the medical practitioner includes at least one applicable diagnosis code corresponding to at least one applicable medical treatment rendered to said patient. Upon receipt by the Informediary, the claim is examined to determine if at least one diagnosis code corresponds to an applicable medical diagnosis found in a database of applicable medical diagnoses. If a corresponding applicable medical diagnosis is present, then a notice is sent by the Informediary to the medical practitioner. The notice sent to the medical practitioner includes the instructions necessary for accessing a medical practitioner Website. Once the medical practitioner gains access to the Website, the medical practitioner will have access to EBM treatment guidelines (if one exists) relating to the medical diagnosis/diagnoses of the patient. Thereafter, the medical practitioner declares/demonstrates adherence or provides a reason for non-adherence to the EBM treatment guideline (if one exists), agrees to allow the patient to confirm/rate the medical practitioner's declaration/demonstration of adherence or reason for non-adherence to the EBM treatment guideline, and then prescribes educational material in the form of information therapy to the patient relating to the medical diagnosis/diagnoses through the Website application. The prescribed information therapy includes instruction for the patient to self-manage his/her medical condition, guidelines for healthy behavior, and a means to assess/determine/test the patient's understanding (health literacy) of the educational material. Additionally and alternatively, the medical practitioner rates patient adherence to the prescribed Ix and recommended treatments and healthy behaviors. Following the prescription of Ix, the Informediary automatically generates a notice to the patient directing the patient to access the Website. Once the patient accesses the Website, the Website provides the patient with the means to access the educational material relating to his/her medical diagnosis/diagnoses. The method further provides for the monitoring of the patient's access of the medical information. The Website further provides a knowledge exam/assessment/test designed to measure patient comprehension of the medical diagnosis, how his/her doctor (medical practitioner) should be treating the diagnosis, and how the patient can/should self-manage his/her condition. Provided that the patient takes the exam or declares his/her understanding, the Website will automatically score the knowledge exam and it will provide the patient with the option of (or require) forwarding (posting for access) the knowledge exam or declaration of understanding results to the medical practitioner. The patient is also asked to indicate their personal adherence or reason for non-adherence to recommended care and healthy behaviors, to report their health status, to agree to allow his/her medical practitioner to confirm/rate/acknowledge the patient's knowledge exam/declaration and declaration/demolition of adherence (or reason for non-adherence) to recommended care and healthy behaviors, and to rate their medical practitioner's performance against the recommended care. Finally, the patient is provided with the option of authorizing the compliance rating assigned by his/her medical practitioner to the patient's health plan and/or employer for the purpose of determining a financial or other types of reward.

In a further embodiment of the current invention, the patient is provided with the option of rating (or is required to rate) the medical practitioner's adherence or reason for non-adherence to EBM treatment guidelines or other accepted care corresponding to the patient's diagnosis. Following review of the prescribed Ix educational material, the patient is asked to rate the medical practitioner's care against the Ix educational material. This rating ideally does not, though it may, directly affect that medical practitioner's reward or compensation on a case-by-case basis. However, it does begin to build an overall clinical performance rating for that medical practitioner. This can be used to help individual medical practitioners measure their performance against their peers. Poor ratings can be used in peer review. This embodiment of the invention allows and encourages medical practitioners the freedom to use their clinical judgment to deviate from a guideline while receiving the maximum financial reward, provided the medical practitioner selects or supplies a reason for the deviation and agrees to allow the patient to concur with/acknowledge/rate the medical practitioner's reason for non-adherence. Preferably, the ratings provided by the medical practitioner and the patient would be obscured from each other to help protect the doctor-patient relationship with each party having the option of releasing his/her rating to the other party.

Still further, the current invention provides a method for delivering healthcare services through a web-based/telephonic interface, interactive provider-patient incentive (reward) system. The system of the current invention comprises a Website operated by an Informediary and having a medical practitioner portion/section and a patient portion/section. The medical practitioners portion is programmed to be accessed directly by the medical practitioner during the patient encounter (t)e "real-time" method) or to receive a claim submitted by the medical practitioner after the patient encounter containing standard codes for the patient's diagnosis(es) and medical services rendered by the medical practitioner (t)e "after-the-fact" method). The Website compares the medical diagnosis(es) entered by the medical practitioner directly into the Website during the patient encounter or from a coded claim submitted by the medical practitioner to a database of medical diagnoses.

Preferably, the system of the current invention will provide suitable incentives to both the patient and the medical provider to bring about a change in behaviors resulting in an improved standard of care and an improved level of healthiness that leads to better clinical outcomes for the patient and lower overall costs for the healthcare system. Additionally, the improved method for delivering healthcare aligns the interests of all the key stakeholders in the healthcare industry. These key stakeholders are generally identified as medical providers (physicians/doctors/healthcare or medical service providers/medical practitioners/clinicians/providers/hospitals), patients (healthcare consumers/heaith plan members/beneficiaries), and health plans (self-insured employers/health insurance companies/govemmental health programs such as Medicare, Medicaid, Veterans Administration, and Indian Health Service/health plan sponsors). For the purposes of this discussion, the current invention focuses on services delivered by a medical practitioner such as a physician; however, the methods of the current invention apply equally well to other types of clinicians such as physician assistants (PAs), nurse practitioners (NPs) and other healthcare providers recognized by patients as trusted and respected healthcare authorities.

To encourage medical practitioner participation in the method of the current invention, medical practitioners will be financially rewarded (compensated) for each patient encounter when the medical practitioner accomplishes the following tasks for each treated diagnosis: 1) if available, consider EBM and other recommended treatment guidelines (and other performance standards) and indicate adherence or reason for non-adherence to the guideline; 2) prescribe educational material in the form of information therapy to their patient (not optional for a financial reward); 3) rate/acknowledge the patient compliance to recommended care for each diagnosis; 4) agree to allow the patient confirm/rate the medical practitioners declaration of adherence or reason for non-adherence to the guideline or recommended care; 5) respond appropriately to patient responses on the Website to include warnings/alerts of patient medical issues; and 6) congratulate the patient for achieving health objectives.

As an encouragement to respond to Ix prescriptions and to live a healthy lifestyle, the methods of the current invention financially rewards patients for completing the following tasks: 1) read the medical educational material prescribed to them on the Website concerning their health condition, recommended (EBM) care and other pertinent performance standards; 2) answer questions presented on the Website to demonstrate their understanding of the educational material; 3) indicate their adherence or reason for non-adherence to the recommended (EBM) care and healthy behaviors; 4) report (or have health monitoring devices report) their health stat s such as weight, blood pressure, blood sugar, and resting heart rate; 5) authorize access to pharmacy records to verify that their prescriptions have been tilled and they have passed a drug literacy assessment, and/or request verification that they have successfully participated in a health assessment or screening program, and/or authorize access to lab and other test results, and/or authorize access to a readiness to change program indicating their participation and accomplishments, and/or request verification that they have seen or scheduled to see a medical specialist or have successfully completed or scheduled to complete other recommended therapies, and/or release information indicating they have updated a personal health record with pertinent information and request his/her medical providers to use the personal health record in his/her treatment to achieve coordination of care and to prevent duplication of care, and/or provide access to an advance directive, and/or participate in a pre-authorization certification of expensive tests and services (such as surgeries and hospitalizations) through the Website to prevent unnecessary procedures and insure better clinical outcomes, and/or demonstrate/declare their healthy behavior or adherence by any other means to other performance standards prescribed by their physician or offered by their health plan; 6) agree to allow their medical practitioner to acknowledge/confirm/rate their adherence to any and all prescribed or offered performance standards; 7) after acknowledging their medical practitioner's recorded responses to the Website question(s) about adherence or reason for non-adherence to a recommended treatment or performance standard, and taking into consideration the educational material they have just read on the method's Website, rate/confirm/refute their medical practitioner's adherence or reason for non-adherence to the performance standard; and/or 8) as an option, elect to have (authorize that) their medical practitioner's rating of the patient's adherence to recommended care and healthy behaviors (or other performance standards) be used to determine their financial reward or health status (this election by the patient further reinforces the Program's strategic checks and balances ("doctor-patient mutual accountability") because patients are aware that this election will cause the Program to compare their personal health adherence responses against their medical practitioner's rating of their health compliance, and if the compliance indicators between the patient and the medical practitioner match, then the Program would indicate that the patient is be eligible for an additional financial reward from their health plan).

In the preferred embodiment of the current invention, the intermediary should select the Program's treatment guidelines, educational material, and other types of medical practitioner and patient performance standards, as well as the reason for non-adherence as an independent party to prevent biasing the Program in favor of any of the stakeholders. With regard to the medical practitioner's reason for non-adherence, the reasons must be appropriate/legitimate, and therefore the reasons are established as the following:

Co-morbidity

Emergent condition

Pending lab or other test results

Contraindicated because: (requires the medical practitioner to explain)

Using an advanced treatment with the patient's consent

Patient declines for financial reasons

Patient declines for other reasons: (requires the medical practitioners to explain)

Guideline in error or out of date: (requires the medical practitioners to explain)

The patient's reasons for non-adherence are established as:

I believe my doctor has mis-diagnosed my condition: (requires the patient to explain and recommends the patient consult with his/her physician)

I am afraid of the recommended treatments—(recommends the patient consult with his/her physician)

I can't afford the recommended treates (recommends the patient consult with his/her physician)

I believe the treatments are inappropriate or unnecessary: (requires the patiento explain and recommends the patient consult with his/her physician)

I have recovered from my illness

I have chosen not to follow the recommended treatments because: (requires the patient to explain and recommends the patient consult with his/her physician)

The healthcare delivery methods of the current invention will be described with reference to FIGS. 1, 2 and 3. To aid in identification of the various steps of the current invention, identifying numbers are provided for selected portions of the process. Electronic communications, such as but not limited to Internet, e-mail, provide the most efficient means for practicing the methods of the current invention. However, the methods of the current invention may be readily adapted to a telephone or telephonic service, standardize electronic data interchange, text messaging; traditional mail, faxes and other hard copy communications or a blend of electronic communication and traditional hard copy communications.

Figure 2:
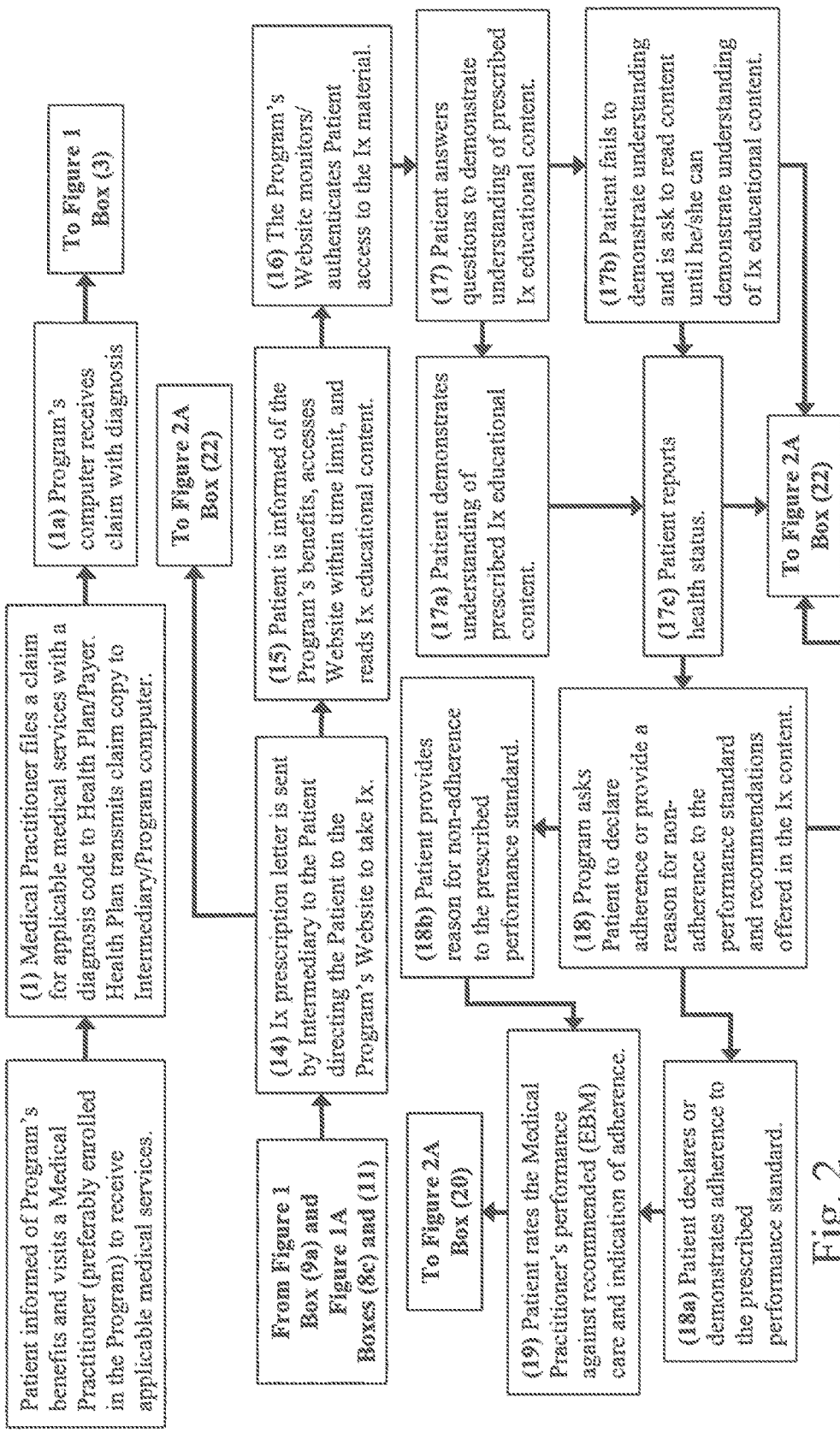

FIGS. 1 and 2 provide flow charts of the method for providing healthcare. FIG. 3 provides an illustrated description of the preferred embodiment of the current invention. FIG. 1 outlines an embodiment of the current invention as it relates to the medical practitioner's portion of EBM and Ix. FIG. 2 outlines the patient's portion of an embodiment of the current invention. While shown in step wise format, those skilled in the art will recognize that various portions of the process can be moved earlier and later in the charts. The methods of the current invention are designed to provide flexibility and adaptability depending on the desires of the local health plan. The format of the current invention may be adapted by any form of health plan. As used herein, the term "health plan" refers to the organization underwriting the cost of the healthcare insurance coverage and managing the healthcare delivery system, and may include self-insured employers, health insurance companies (and their customers to include employers and individuals who purchase health insurance coverage managed care plans, healthcare CO-OPs, U.S. governmental programs such as Medicare, Medicaid, Veterans Administration, military, state and Federal employees, and Indian Health Service, and all types of national health services and systems in other countries.

As shown in FIG. 1, the method of the current invention begins with educating the patient and the medical practitioner on the benefits of the current invention (referred to herein as "the Program"), to include why and how the methods of the Program work. Medical practitioners are made aware of the Program by a variety of means to include organized meetings, targeted mailings and telephone contact, or with the aid of a local medical provider organizations (medical provider organization licensee) contacted to sponsor the Program in a marka, or patients who inform or ask their medical practitioner to participate. Medical practitioners are directed to the Program's Website to enroll online. Prior to receiving treatment, the patient can identify a medical practitioner that participates in the Program, but receiving medical service from an enrolled and participating medical practitioner is not a requirement in order for the Program to work. Typically, the Program will be administered by an independent intermediary that operates the Website and administers the Program's computer that hosts the Website and manages the Program's databases and electronic interfaces with the health plan and suppliers of content and services used to operate the Program. The intermediary sells Program access and service agreements to health plan sponsors. Health plan sponsors "bolt-on" the Program to their actual health plans, which in the case of self-insured employers may be managed by an independent third party administrator (TPA) or an administrative services only (ASO) provider. (Though it is not recommended, in another embodiment of the current invention, the health plan can also function as the intermediary) It is the intermediary that will typically license medical provider organizations (such as a medical group practice, independent practice association or IPA, or a physician-hospital organization or PHO) to administer provider relations and promote the Program in a market. An example of these relationships is as follows; the independent intermediary setts a user license and service agreement to the health plan. The health plan may comprise a self-insured employer. The health plan's beneficiaries to include a self-insured employer's covered employees and dependents, collectively, represent the health plan's members. The health plan supplies, typically electronically, a list of eligible members to the intermediary. The intermediary stores the eligible members listing (file) in the Program's database. This file of eligible members is updated, typically electronic, by the health plan periodically.

When a member seeks healthcare, they are described as patients. A patient seeking medical services presents themselves to a medical practitioner as a member of the health plan covered by the Program. Subsequently, the medical practitioner provides healthcare services to the patient. The medical practitioner can voluntarily elect to participate in the Program with each service encounter with a covered patient. Preferably, the medical practitioner elects to participate by accessing the Program's Website at the time of service (enrolls in the Program if he/she has not done so previously) and enters pertinent patient information and diagnosis(es) information preferably as a standardized diagnosis(es) code(s). (This preferred time of service method of practicing the Program is referred to as the point-of-service-initiated or "POSI" real-time version as opposed to the claim initiated or "CI" after-the-fact version, which is described later,) As shown in FIG. 3, the Program's software application compares the patient and diagnosis(es) information to the Program's database stored on the intermediary's computer. If the Program's software finds a patient information match in the Program's database and there is available EBM or recommended treatment guidelines (a medical practitioner performance standard) and patient educational content (material) and/or patient performance standard related to the diagnosis(es) in the database, then the Program displays the treatment guideline and educational content (and any other performance standards) to the medical practitioner on the Website Refer to FIG. 3, Step #6). The Website is interactive. As such, if an EBM or recommended treatment guideline is available, the medical practitioner considers the guideline and indicates/declares/demonstrates adherence or reason for non-adherence to the guideline on the Website. In the process, the medical practitioner agrees to allow patient to or acknowledges that the patient will confirm/rate/concur the medical practitioner's declaration/demonstration of adherence or reason for non-adherence to the guideline. If educational content and a patient performance standard are available, the medical practitioner selects or searches for the preferred content (and/or other patient performance standard) and orders an Ix prescription (and/or other patient performance standard) for the patient on the Website. Optionally, the medical practitioner is asked to rate the patient's compliance to EBM or appropriate care for each presenting diagnosis. Again, the medical practitioner may be asked to consider or initiate other types of performances standards such a pre-authorization certification for certain heavy cost medical service, or a pharmacy benefits management service to include electronic prescriptions and lower cost therapeutic substitutions, or the updating of the patient's web-based personal health record, etc. The patient and diagnosis(es) information, the medical practitioner's response(s) to guideline adherence, the agree to allow the patient to confirm the medical practitioner's adherence (or non-adherence), the Ix prescription order, the medical practitioner's rating of the patient's compliance, and responses to other performance standards are stored in the Program's database for subsequent processing to determine the medical practitioner's rate of compensation by the intermediary.

The Ix prescription or other performance standard order can be printed by the medical practitioner at the time of service so it can be handed to the patient, or these documents can he mailed or e-mailed to the patient. Alternating, the medical practitioner may choose to postpone participating in the Program until after an insurance claim for reimbursement of the medical services is submitted to the health plan (see description of the CI after-the-fact version below). Therefore the Program's processes can be initiated at the time of service by the medical practitioner accessing the Program's Website or it can be initiated by filing an insurance claim for normal medical services reimbursement.

Following treatment of the patient, the medical practitioner files an insurance claim for medical services reimbursement with the health plan administrator. Preferably, the medical practitioner files the claim electronically (FIG. 1, Step #1). The medical claim contains information commonly found on current claim forms such as the patient's name, the medical practitioner's name, a primary medical diagnosis, secondary diagnoses) and the service provided by the medical practitioner. Preferably, the medical diagnosis and the medical services are identified by a usual and customary diagnosis and medical services codes, and the diagnosis(es) is appropriately linked to the corresponding medical service(s). The health plan simultaneously processes the claim (as usual) and also forwards a copy of the claim to the intermediary (refer to FIG. 1, FIG. 2, Step #1, and FIG. 3, Step #10).

Upon receipt of the claim, the patient and diagnoses information are compared by the intermediary to any matching information in the Program's database. Matches then determine if the claim lists eligible medical services (referred to as "applicable medical service(s)") contained in the Program's database. If the claim contains applicable medical services (FIG. 1, Step #1), then the medical practitioner's stored responses to the Website queries concerning guideline adherence, (or reason for non-adherence), Ix and other patient performance standards prescriptions, agreement to allow patient to or acknowledge patient will confirm/rate medical practitioner's adherence (or reason for non-adherence), and medical practitioner's confirmation of the patient compliance for the diagnosis(es) and other performance standards linked to the applicable medical services are taken into consideration in determining, the medical practitioner's rate of reimbursement (compensation) as described herein.

Figure 1A:
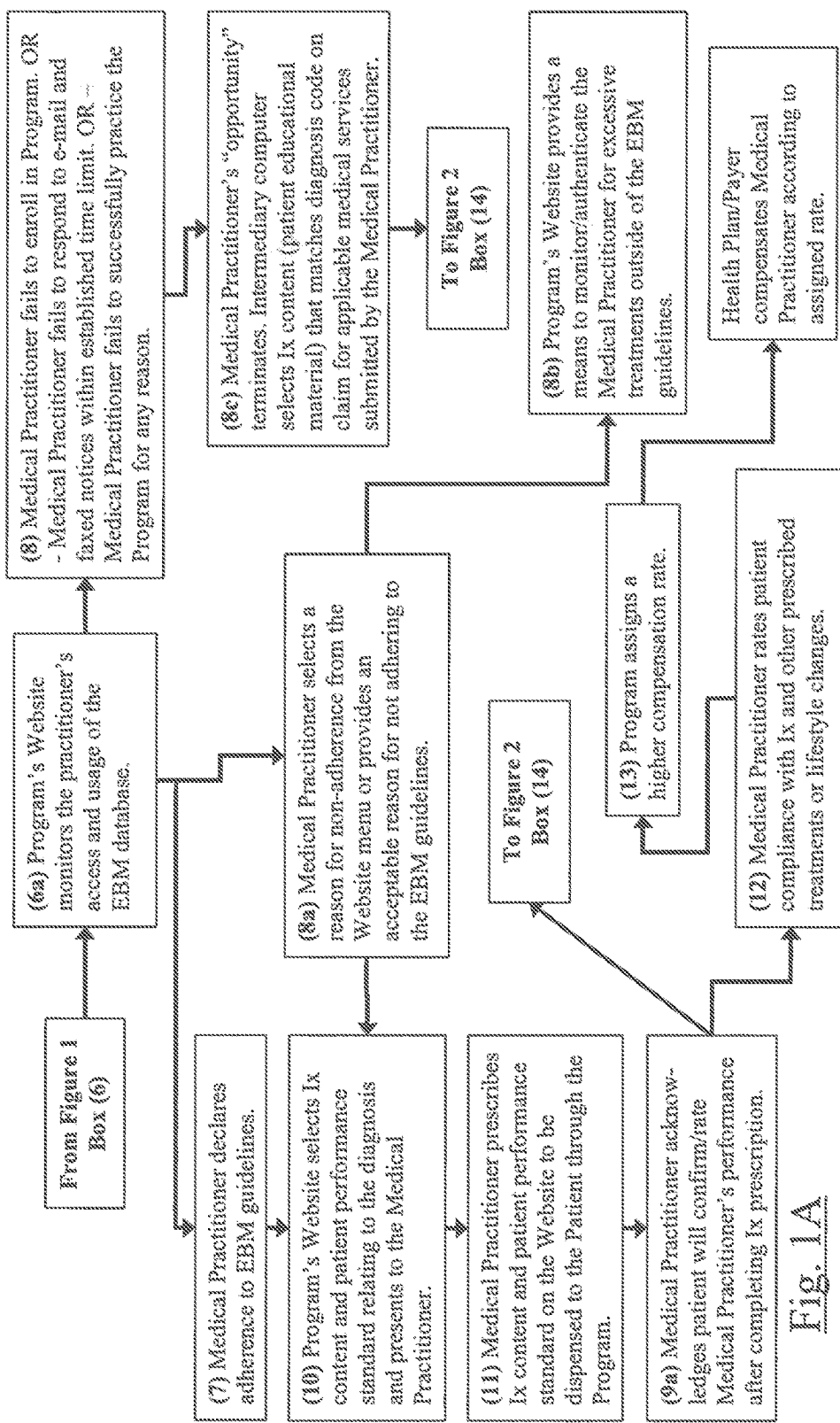

If the diagnosis code does not match an accepted guideline in the Intermediary's database FIG. 1, Step #9), the intermediary's computer selects information therapy content that matches the diagnosis code and sends a notice to the service provider. The service provider responds to the notice by accessing the Program's Website. The service provider accepts the information therapy provided by the program or researches and selects information therapy on the website to be prescribed and dispensed to the patient through the program. Depending on the compensation requirements of the health plan and intermediary, the service provider may be required to acknowledge or confirm a patient indication of adherence, and then the Program either assigns an intermediate compensation rate or an Ix prescription letter is sent by the intermediary to the patient (FIG. 2, Step #14), Medical practitioners must submit an insurance claim for medical service reimbursement within a time limit or they will not be eligible for the higher rates of reimbursement or any compensation associated with the Program for that patient encounter. (As indicated in FIG. 1A, Step #8, missing the time limit for filing a claim would not necessarily affect future opportunities to practice the Program.) If information supplied by the medical practitioner at time of service is not matched to a claim within a certain period of time, then the Program may send a notification/warning to the medical practitioner that the claim filing time limit about to expire.

Alternatively, if the medical practitioner did not access the Website or respond to the Website queries at the time of service (the POSI real-time version), then once the claim for medical services are forwarded to the Program's (intermediary's) computer system, the system will not identify matching patient and diagnosis information (refer to FIG. 1 and FIG. 1A). If this is the case, then the computer compares the claim information to the Program's database for applicable diagnoses. If the claim contains an applicable diagnosis, then the computer determines if the diagnosis is linked to an applicable medical service. If this is the case, then the computer automatically sends a notification (preferably email and/or fax) to the medical practitioner informing him/her that there is a Program "opportunity" ("AOI opportunity") available (3). (This after-the-fact method defines the claim initiated or CI version of the Program and diagrammed in FIG. 1 and FIG. 1A.)

The notification sent to the medical practitioner advises the medical practitioner to access the medical practitioner's portion of the Program's Website containing EBM guidelines or other healthcare quality improvement, patient education material, and other cost control methods (collectively referred to as performance standards). The Program Website is preferably a secure website requiring input of the medical practitioner's password to gain access to the data contained therein. Alternatively, these access codes may be transmitted by a separate email or otherwise provided to the medical practitioner. (The method for gaining access to the Website is not critical to the current invention.)

For the purposes of this disclosure the term website refers to the Program's Websites. The Program's Websites may or may not be located on a central server at the intermediary. Further, the patient and medical practitioner portions of the Program's Websites are not necessarily contained on the same computer system, but may be maintained by health plan's computers or multiple independent intermediaries. As used herein, the medical practitioner portion of the Program's Website will preferably be utilized by all parties authorized to access the medical practitioner's portion of the Website, including but not limited to nurses, nurse practitioners, physician assistants and other care providers, Upon entry of the appropriate codes or passwords at the Website (FIG. 1, Steps #2 and #4 and FIG. 3, Step #5 and #6), the Website identifies the names of patients, the dates and types of services provided, the medical diagnoses and related medical services for the accessing medical practitioner or authorized assistant (delegates can be set-up in the Program's computer, provided the delegate is approved and supervised by a licensed medical practitioner). The Website also provides the available EBM guidelines or other healthcare quality improvement and cost control methods (performance standards) corresponding to each diagnosis. Preferably, the medical practitioner reviews and confirms the appropriateness of the information found on the Website (FIG. 1, Step #5).

The Programs Website is interactive. As such, it queries the medical practitioner concerning adherence or reason for non-adherence to EBM guidelines or other healthcare quality improvement and cost control methods (performance standards) for the diagnoses (FIG. 1, Step #6 and FIG. 3, Step #7), the agreement to allow the patient to or acknowledgment that the patient will confirm/rate the medical practitioner's adherence or reason for non-adherence to the performance standards, the prescription educational material as Ix to the patient, and patient compliance with the prescribed treatment and guidelines on living a healthy lifestyle and methods for controlling/managing the patient's medical condition (FIG. 1A, Step#12 and FIG. 3, Step #9). The medical practitioner's response to the queries will determine the reimbursement rate used to compensate the medical practitioner for services rendered on each claim associated with a Program opportunity. If the medical practitioner responds to the queries concerning patient compliance, prescription of Ix to the patient, declaration/demonstration of adherence or reason of non-adherence to EBM guidelines or other healthcare quality improvement and cost control methods (performance standards), and the agreement to allow the patient to or acknowledge that the patient will confirm/rate the medical practitioner's adherence or reason for non-adherence to the performance standards are appropriate (FIG. 1A, Step #13 and FIG. 3, Step #12), then the Website automatically direct compensation to be made according to a higher payment (practitioner reimbursement) rate/scale (FIG. 1A, Step #13). Preferably, the highest rate of medical practitioner compensationment) is selected when the medical practitioner practices the method on a real-time basis using the POSI version of the Program. (Timelines can be important in delivering information therapy and other services initiated through the Program to the patient. Therefore, the highest rate of medical practitioner compensation is typically assigned when the POSI version of the Program is practiced.) Alternatively, the highest rate of compensation can be assigned in instances where the medical practitioner has indicated adherence or reason for non-adherence to a recommended treatment guideline, agreed to allow the patient to or acknowledged that the patient will confirm/rate the medical practitioner's adherence or reason for non-adherence to the performance standards, prescribed Ix for the patient (FIG. 1A, Steps #10 and #11) and has rated patient compliance (FIG. 1A, Step #12 and FIG. 3, Step #9). (It should be noted that additional medical practitioner compensation can be earned through the Program as other performance standards are added to achieve the intended objectives.) Typically, a secondary level or lower rate of compensation (payment) is assigned. (selected) when the medical practitioner practices the after-the-fact CI version of the Program. Alternatively, the secondary level of compensation can be assigned (selected) when the medical practitioner has prescribed Ix for the patient and has rated patient compliance, but no treatment guideline is available or some other diminished level of service is provided.

As noted above, the Website also queries the medical practitioner concerning the patient's compliance with health recommendations and EBM guidelines, Ix and any lifestyle activities necessary to improve the patient's wellness. Preferably, the Website will provide the medical practitioner with the opportunity to rate patient compliance with the recommended treatment and behaviors using the following terms: Compliant, Mostly Compliant, Somewhat Compliant, Mostly Non-compliant, Non-compliant and Non-applicable. Alternatively, the patient compliance rating terms may be: Compliant and No Response. No Response may mean partially compliant, noncompliant, or non-applicable. To receive the highest compensation level for the services provided, the medical practitioner may need to respond to the request for a patient compliance rating. The ratings provided by the medical practitioner will be stored by the Program awaiting a response by the patient to the prescribed Ix. However, the patient will not have the ability to see the medical practitioner's rating unless the medical practitioner has selected the option to permit the patient to view the rating.

Typically, the medical practitioner must access the interactive Website within 48 to 96 hours of receipt of the after-the-fact, CI notification in order to qualify for the higher payment rate scale. In the preferred embodiment, the medical practitioner is required to respond to the notice within 48 to 96 hours or two to four business days. If the medical practitioner does not respond within the indicated period of time (FIG. 1A, Step #8), then the Website will direct compensation to be made according to a lower (or lowest) rate scale or to cause the Program opportunity for the medical practitioner to expire resulting in no compensation to the medical practitioner association with the Program for that opportunity (FIG. 1A, Step #8c).

As previously indicated, the Program's Website is interactive. To provide the maximum flexibility and greatest possibility of improved clinical outcome for the patient, the method of the current invention does not rigidly limit the medical practitioner only to the EBM guidelines in order to receive the highest degree of compensation. Rather, the Program's Website provides the medical practitioner with the option of indicating the treatment falls outside of the guidelines while explaining the reason for prescribing treatment outside of the guidelines. Provided that the medical practitioner completes the section describing an appropriate reason for non-adherence to the recommended treatment (FIG. 1, Step 18a), the Program's Website will still select the highest compensation level for the medical practitioner. Thus, the present invention avoids the practice of "cookbook medicine" by encouraging the medical practitioner to use appropriate clinical judgment and medical skills when deciding to on whether or not to follow the EBM guidelines. In order for this "anti-cookbook" feature to work, the medical practitioner must agree to allow the patient to confirat/rate/concur with the medical practitioner's declaration/demonstration of adherence or reason for non-adherence to the recommended (EBM) care.

As previously indicated, in the preferred method the medical practitioner must prescribe educational material as Ix for the patient and (alternatively) rate patient compliance with directions/guidelines on living a healthy lifestyle and other methods for controlling/managing the medical condition before becoming eligible to receive payment at the highest or second highest (intermediate) compensation rates.

Again, the medical practitioner is not required to indicate compliance with the EBM guidelines; however, failure to respond within 48 to 96 hours or indicating non-adherence without providing an appropriate reason for treatment outside of the EBM guidelines can have a negative financial impact on the medical practitioner. Specifically, these actions will trigger the intermediary's computer system to select the lowest possible payment scale for the medical practitioner's services (FIG. 1A, Step #8c) or terminate that "opportunity" for the medical practitioner to earn any additional compensation at all. If the medical practitioner fails to prescribe educational material as Ix for the patient, then the Website will direct the selection of the lowest payment scale for compensation of the medical practitioner or not compensation the medical practitioner for that "opportunity" at all. Furthermore, if the medical practitioner fails to participate in the Program for any given "opportunity" or to satisfactorily complete the steps that are required of a successful participation for any given "opportunity" as established by the health plan sponsor (in consultation with the intermediary) and adjudicated by the intermediary within the specified time limit, then the medical practitioner's opportunity will expire and he/she will not be compensated, As a result of the medical practitioner's failure to successfully participate in the Program for any given "opportunity," the patient's "opportunity" to participate may or may not be affected in accordance with Program requirements established by the health plan sponsor in consultation with the intermediary. Typically, the patient's "opportunity" to participate is not affected. In this case, the diagnosis listed on the medical service claim for payment submitted by the medical practitioner provides the means by which the intermediary's computer system can automatically generate an Ix prescription letter, email or other type of notification to the patient that informs the patient of chance to participate in the Program for said "opportunity." This notification to the patient may inform the patient that the medical practitioner failed to participate in the Program for said "opportunity" or, if it is the case, a series of 'opportunities," As a result, the current invention can promote consumerism by providing patients with important medical service quality information to help them be more discerning in their healthcare choices or to encourage them to urge their medical practitioners to participate in the Program. This method also heightens the current invention's "checks and balances" ("doctor-patient mutual accountability") designed to motivate better health behaviors and healthcare, Thus, the method of the current system provides a financial incentive to the medical practitioner to follow the EBM guidelines or to provide an appropriate reason for deviating from these guidelines, provided the medical practitioner agrees to allow the patient to confirm/rate/concur with the medical practitioner's declaration/demonstration of adherence or reason for non-adherence to the guidelines. Additionally, the method of the current invention provides a financial incentive to the medical practitioner to prescribe Ix to the patient and to rate patient compliance with the prescribed treatment/lifestyle necessary to manage the medical condition. Furthermore, the method of the current invention provides a financial incentive to the medical practitioner to practice the Program on a real-time basis as opposed to after-the-fact. However, the method uses financial incentives to create other perhaps stronger incentives for the medical practitioner to practice the method. These incentives include the medical practitioner's desire to: 1) improve communications with patients; 2) improve the patients' understand of their medical condition and how to self-manage their health; 3) provide a means to help/motivate patients be more compliant to recommended care and adopt and maintain better health habits; 4) increase productivity; 5) gain a degree of medical malpractice risk management; 6) have access to the latest and best methods for treating diseases and injuries; 7) incorporate other beneficial performance standards; and last but not least 8) prevent patients and others from thinking he/she practices inferior healthcare or, worse yet, learn that tie/she is not truthful about what kind of medicine he/she practices. This final ($8^{th}$) incentive (i,e., motivator) describes one of the checks and balances that is unique to the current invention. In effect, the medical practitioner is aware that the patient earns a financial reward for becoming qualified to rate the practitioners adherence to and performance against high and beneficial standards. The medical practitioner is also aware that patients' ratings will be aggregated and compared to the medical practitioner's peers. This is a powerful incentive that encourages medical practitioners to participate in the Program and to practice medicine that is recommended by the medical profession or to provide appropriate reasons for non-adherence. In general, treatment according to the EBM guidelines and appropriate treatment outside of the guidelines coupled with patient compliance with treatment protocols and a healthy lifestyle will produce better clinical outcomes. Further, the prescription of educational material as Ix to the patient empowers the patient to be more compliant with their medical practitioners treatment orders and instructions, leading to improved clinical outcomes. Additionally, the patients access to educational material and the process of assessing the patient's understanding of that material provides the patient with the empowerment and additional motivation to improve the medical practitioner's medical condition, which leads to improved medication adherence and other therapies, which leads to a decrease in expensive services such as hospitalizations. Thus, the current invention provides a method for improving clinical outcomes, promoting healthiness, which leads to reduction in healthcare costs. Clearly, the current invention integrates the activities of the patient and medical practitioner by encouraging the incorporation of EBM, Ix and other beneficial performance standards by combining financial incentives with powerful psychosocial motivators.

In order to achieve medical practitioner participation and adherence while preventing fraud and abuse, the Program's Website software applications provide the means to monitor and audit the medical practitioner. In one aspect, the Website provides the means for tracking the medical practitioner's access to the Website. This tracking mechanism provides an indication of the medical practitioners use of the EBM guidelines. For example, the Program's Website tracks the access time for each webpage reviewed, if the time of usage for each page does not meet a predetermined minimum, then the medical practitioner may be questioned concerning the legitimate usage of the EBM guidelines. However, the predetermined minimum time period for accessing a webpage is not a rigid requirement Rather, the minimum access time period may vary from practitioner to practitioner and from diagnosis to diagnosis based on various parameters such as but not limited to the medical practitioner's area of expertise and experience and whether a particular webpage has been previously reviewed and/or printed by the medical practitioner. If a new medical treat e t is established as recommended by the medical community and is new in a EBM treatment guideline, then the invention's Website application may prevent the medical practitioner from exiting that webpage or from receiving a higher rate of reimbursement or additional compensation until the medical practitioner "drilis-down" into the application to learn about this new medical development, advancement, and/or treatment. The Program can also administer exams to verify medical practitioner compliance and to prevent fraud and abuse. However, the strongest means to prevent fraud and abuse rests with the Program's "doctor-patient mutual accountability" feature. Patients are educated by an independent expert source about how their medical practitioner should care for their medical condition, and then patients are immediately queried about how their medical practitioner is performing against what they have learned, and how consistent the medical practitioner's declaration of adherence is to, again, what they have learned. This represents a fair and appropriate way to rate medical practitioner performance (especially compared to web-based. satisfaction surveys) that balances the interests of the medical practitioner with the interests of the patient and the health plan sponsor.

In another aspect, the Website provides the means for monitoring the frequency of treatments outside of the EBM guidelines (FIG. 1A, Steps #8 and #8a). Thus, the current invention provides health plans using the methods of the current invention with the ability to audit medical practitioners who may not be using the best treatments for their patients by using treatments outside of generally accepted procedures. As indicated above, the methods of the current invention are flexible and can be adjusted for individual practitioners on the basis of their practice area and experience and also adjusted to incorporate additional types of performance standards linked to specific incentives (as long as one or more incentive is interactive involving the checks and balances between the medical practitioner and the patient facilitated by the current invention) to achieve the objectives of better health and better and more affordable healthcare. The current invention's capability to adjust and expand performance standards and incentives to achieve specific objectives is referred to as "precision-guided incentives and performance standards."

The foregoing steps of the method of the current invention provide an incentive to the medical practitioner to comply with the treatments specified in the EBM guideline database and to rate patient compliance with prescribed reatment/satifestyle necessary to manage the medical condition. The current invention is design to accommodate EBM guidelines from any unbiased, independently derived, highly reputable source that has used generally accepted testing protocols to establish recognized level of proof. Therefore, the Program does not endorse any one source of guidelines, content or medical intervention. However, the Program is constantly seeking the best possible guidelines, content and medical interventions to integrate with the current invention.

Providing an incentive to the medical practitioner addresses only one part of the total cost of healthcare. In order to further improve the patient's clinical outcome, promote healthiness, and enhance healthcare cost control, the patient must also play a role. Accordingly, the methods of the current invention provide an incentive to the patient to take a pro-active approach to recover from and prevent adverse medical conditions.

With reference to FIG. 2, the method of the current invention provides the medical practitioner with the option of prescribing Ix and other performance standards to the patient (F 1A, Step #11). In the preferred embodiment, the method encourages the medical practitioner to prescribe Ix and other performance standards to the patient by rewarding the medical practitioner with additional compensation. Preferably, the medical practitioner wilt prescribe the Ix and other performance standards at the same time the medical practitioner is responding to the Website's inquiry regarding medical practitioner's compliance with EBM guidelines for the prescribed medical treatment. The prescribed Ix will normally be provided via an Internet website or a telephone/telephonic service. For the remainder of this discussion, the source for the prescribed Ix and other performance standards wilt be referred to as the Program's Website; however, other sources of information are within the scope of the present invention.

If the medical practitioner prescribes Ix for the patient, then a notice in the form of an e-mail, fax, text message, letter or other similar communication will be sent automatically to the patient by the Program or handed to the patient at the time of service by the medical practitioner (or the practitioner's staff). This patient notification (FIG. 2, step #14) may contain the medical information or more preferably the notice will contain the information about the benefits of the Program, including the financial incentives available to the patient, and instructions on how to gain access to the Program's Website. The notification will also inform the patient that his/her participation in the Program is completely voluntary.

As mentioned previously, if the medical practitioner fails to participate or fails to successfully complete an "opportunity," then the diagnosis listed on the medical service claim for payment submitted by the medical practitioner provides the means by which the intermediary's computer system can automatically generate the notification to the patient (FIG. 1A, Step #8c) that informs the patient of his/her chance to participate in the Program for said "opportunity."

Upon receipt of the correspondence/notification, the patient will be directed to the patient portion (section) of the Program's Website. Once online, the Website will inform the patient (FIG. 2, Step #15) that he/she can earn a financial incentive and gain valuable health information by successfully completing the following tasks: 1) read the educational material presented to them on the Website about his/her health condition, recommended (EBM) care, other pertinent and beneficial performance standards (FIG. 2, Step #15); 2) answer questions presented on the Website to demonstrate his/her understanding of this material (health literacy assessment) (FIG. 2, Steps #17, #17a, and #17b); 3) declare his/her adherence or reason for non-adherence to the recommended (EBM) and appropriate care or other beneficial performance standards (FIG. 2, Steps #18, #18a, and #18b); 4) report (or have health monitoring devices report) his/her health status such as weight, blood pressure, blood sugar, and resting heart rate (FIG. 2, Step #17c); 5) authorize to access pharmacy records to verify that prescriptions have been filled, and/or request verification that the patient has successfully participated in a health assessment and/or screening program, and/or release information that he/she is participating in a readiness to change program, and/or authorize access to lab and other test results, and/or request verification that the patient has seen or is scheduled to see a medical specialist or has successfully completed or scheduled to complete other recommended therapies, and/or release information concerning his/her participation in therapeutic social networking, and/or authorize or affect the population of a personal health record with pertinent information and request his/her medical providers to use the personal health record in his/her treatment to achieve coordination of care and to prevent duplication of care, and/or participate in a pre-authorization certification of expensive tests and services (such as surgeries and hospitalizations) through the Website to prevent unnecessary procedures and insure better clinical outcomes, and/or release an advance directive, and/or demonstrate his/her healthy behavior by any other means; 6) after acknowledging their medical practitioner's responses to the Website question(s) about adherence or reason for non-adherence to a recommended (EBM) treatment or other performance standards (and taking into consideration the information he/she have just read on the method's Website), confirm/rate/concur with his/her medical practitioner's declaration/demonstration of adherence or reason for non-adherence to the performance standard (FIG. 2, Step #19); and 7) agree to allow his/her medical practitioner to have access to his/her health literacy assessment and declaration/demonstration of adherence or reason for non-adherence to the prescribed treatments and Ix (or other performance standards) (FIG. 2A, Steps #19a, #20a, and #20b). (This agreement by the patient reinforces the Program's strategic checks and balances ("doctor-patient mutual accountability") by making the patient aware that someone he/she respects and trusts when it comes to his/her health, namely his/her medical practitioner, has access to (and may rate the patient on) their health literacy assessment and declaration/demonstration of adherence or reason for non-adherence to Ix and other performance standards creates powerful motivation for the patient to improve and maintain good health behaviors. The Program is also able to compare the patient's declaration/demonstration of compliance responses against his/her medical practitioner's rating of his/her health compliance. If the compliance indicators between the patient and the medical practitioner match, then the Program would indicate that the patient is be eligible for an additional financial reward from his/her health plan.)

With reference to FIG. 2, the patient is expected to review the health educational material made available by the Program's Website (FIG. 2, Step #15). The review of the prescribed educational material as Ix is supplemented with a questionnaire to be completed by the patient to assess the patient's understanding of and adherence to the material. In the preferred embodiment, the Program's Website also provides the means to monitor the patient's access of the Website and completion of the questionnaire (FIG. 2, Step #16). This monitoring aspect provides the network with the means to audit patient compliance with the Ix and other treatment prescribed by his/her medical practitioner. Further, the monitoring system provides the ability to award "points" to the patient for reading the Ix, and for answering the questionnaires that indicate the patient's knowledge and adherence to recommended treatments. As a means to insure compliance and prevent fraud and abuse, the network can designate a minimum period of access time necessary prior to awarding a point for reviewing that section of the Ix. By requiring a minimum time period, the method of the current invention ensures that the patient performs more than a cursory review of the information provided.

Following completion of the questionnaires that tests the patients knowledge and adherence to recommended (EBM) care, establishes the patient's agreement to allow his/her medical practitioner to have access to and rate his/her responses and adherence, and rates his/her medical practitioner performance against recommended (EBM) care; the Website scores the patient's answers and awards points to the patient's account according to the patient's responses. Following scoring, the patient has the option of further reviewing the Ix and repeating the questions or answering additional questions. Thus, the current invention provides the patient with the ability to gain further knowledge of his/her condition while enhancing the number of points awarded to his/her account. Clearly, the comprehensive nature and flexibility of the Program's Website provides the patient with the tools necessary to improve his/her health literacy, emprovement, motivation, and the clinical outcome of his/her treatment and to improve his/her overall general health. Optionally, the health plan may elect to award patients with additional points and financial rewards for reviewing other medical information and accomplishing other performance standards intended to improve health and control cost, that are made available through the Program.

Upon completion of the Ix and indication of adherence and understanding of recommended and appropriate care, agreement to allow his/her medical practitioner to have access to and/or rate/acknowledge/confirm his/her responses to the Website questionnaires, and the rating of his/her medical practitioners performance; the patient is provided with a means for notifying the health plan of the receipt and review of the Ix material. Additionally, the patient will be provided with the option of sharing the medical practitioner's rating of patient compliance with the health plan. Typically, the patient will be provided with separate option boxes or other "clickable" devices on the Website to indicate the patient's desire to share the medical practitioner's compliance rating and to transmit a notice of completion of the Ix material to the health plan and/or employer. In the preferred embodiment of the current invention, the Program Website transmits the patient's actual responses to the questionnaire to the medical practitioner or posts the responses on the Website for access by the medical practitioner. Though these choices are optional to the patient, if the patient elects not to share information, then the health plan will most likely not provide the financial reward(s) to the patient.

In view of the incentives offered by the method of the current invention, the patient will likely request transmission of such notices to the health plan and/or employer. Upon receipt of such notices, the health plan has the option of providing a financial reward to the patient based on the patient's completion of the Ix, declaration/demonstration of adherence or reason for non-adherence to the recommended care, rating of his/her medical practitioner, and the patient's compliance and performance rating of the medical practitioner. In keeping with the flexible nature of the current invention, the financial reward may be granted upon the complaion of each prescribed Ix, indication of adherence, agreement to allow the medical practitioner to have access to (and rate) the patient responses to the website's questionnaires, and the patient's medical practitioner rating portion. Before the intermediary assigns a reward to the patient, the patient declares or demonstrates adherence to the performance standard. The party paying the reward may establish point thresholds for payouts. In the case of point thresholds, the patient's points are accumulated and upon reaching a predetermined level, the financial reward can be paid to the patient.

It should be noted that as with the medical practitioner, the patient's participation in the Program for a given "opportunity" is voluntary and may or may not affect the medical practitioner's compensation for participating in the Program for said "opportunity." In a preferred embodiment of the current invention, the medical practitioner's compensation is not affected by the patient's non-participation.

Typically, a patient will not to earn a financial reward through the Program if the Patient: fails to complete Ix "opportunity" within the established time limit; or fails to pass a health literacy test or demonstrate knowledge of the Ix educational material (though literacy tests in the Program are open book, meaning that patients are asked to read the educational material again when they miss a health literacy question); or fails to report health status; or denies Medical Practitioner access to his or her Website questionnaire responses; or fails score enough points answering Website questionnaires (FIG. 2A, Step #22).

As noted above, the method of the current invention preferably includes the medical practitioner's confirmation of the patient's health literacy and the patient's indication of adherence to recommended treatments. The process of the patient sharing information with his/her medical practitioner and health plan and/or intermediary creates another check and balance that is designed to help improve health behaviors and control costs. In effect, the patient is aware that his/her answers to questions on the Website (or over the telephone) about his/her compliance to performance standards will be available to his/her medical practitioner, health plan, and intermediary for review and authentication. The patient's desire to demonstrate his/her knowledge and compliance to his/her medical practitioner is a strong motivator. The psychological consequence of being found untruthful by someone that the patient trusts and respects, namely the medical practitioner, is a powerful motivator for the vast majority of people.

Obviously, the ideal embodiment of the current invention involves participation of both the medical provider and the patient with each and every "opportunity." However, one important aspect of the current invention that is unique has to do with its functionality and effectiveness when only one of the two parties participates. Since neither the medical practitioner nor the patient knows if the other party will or will not participate in the confirmation of the other's performance, then the psychology that inspires best behaviors inherent to the doctor-patient relationship is present for either party even when the other party does not participate. In the case of the medical practitioner, he/she does not want his/her patients to think or learn that he/she practices inferior medicine after his/her patients complete the Program's information therapy process. However, the medical practitioner will have no way of knowing whether any given patient will participate in any given "opportunity." So to be safe, the medical practitioner is inspired to incorporate EBM (best practices) with every encounter involving a patient covered by the Program just in case. In fact, the Website reminds the medical practitioner of this fact each time he/she is asked to respond to the acknowledgment that the patient will (may) rate the medical practitioner's performance against an independently derived EBM standard. Conversely, the patient does not want his/her trusted and respected medical practitioner to think he/she is health illiterate and/or non-compliant to recommended treatments and healthy behaviors. Again, he/she will have no way of knowing if his/her medical practitioner will or will not review his/her information therapy and declaration or demonstration of adherence responses to the Website questionnaires. Therefore, each time a patient participates in the Program and accepts the Website agreement to allow his/her medical practitioner to have access to his/her Website responses, the Program's psychological motivators are helping to inspire the patient to be healthy and compliant. This is why the medical practitioner's acknowledgment of the patient rating/confirmation and the patient's agreement to allow the medical practitioner to access/rate/confirm "switches" incorporated into the website are such an important feature of the current invention.

Finally, the current invention also preferably provides for patient inquiries of the medical practitioner through the Website, by email or other similar means, during Ix sessions. Thus, the current invention integrates the patient's Ix with the medical practitioner's medical treatment and provides financial rewards to the patient based on completing the educational aspects of Ix as well as financial rewards for adopting a healthy lifestyle and adherence to treatment protocols as recommended by the medical practitioner, for agreeing to allow the medical practitioner to confirm/rate/acknowledge the patient's health literacy and indication of adherence to healthy behaviors and recommended treatments, and for rating their medical practitioner's performance against recommended and appropriate care.

In accordance with the Health Insurance Portability and Accountability Act (HIPAA), the notice to the health plan and any notices to any other third parties will not divulge any protected patient health information unless arrangements have been made to meet HIPAA requirements, In the method, the service provider (medical practitioner/doctor/physician/clinician) and patient may be required to perform an action or physical act to demonstrate as oppose to declare adherence to a performance standard. An action or physical act may or may not be captured on the Website. Since the action or physical act may be captured by the Website, then the service provider and patient would be asked to acknowledge the action or physical act of each other. This implies that the action or physical act can be independently, verified by the acknowledging party and authenticated by the intermediary. An example of a performance standard involving a verifiable action is the service provider electronically prescribing drug therapy to the patient through the Website. Since this action is captured by the Website, the method would ask the service provider to agree to have the patient acknowledge his/her action (adherence to a performance standard), and would preferably involve the patient acknowledging his/her service provider's adherence to the performance standard. Therefore, the terms "declare and confirm" and "declaration and confirmation" are synonymous to "demonstrate and acknowledge" and "demonstration and acknowledgment" when a verifiable action or physical act is involved.

The present invention is designed to allow the health plan and the intermediary to select (or determine a variety or varying amount of performance-based incentives depending upon the level or degree of adherence or performance by the service provider and the patient against a performance standard or multiple performance standards. An example of this feature involves establishing one amount of compensation for the service provider when he/she prescribes information therapy to the patient and an additional (or separate) amount of compensation when he/she uses a drug therapy management system to electronically prescribe pharmacy to the patient. In this case, the intermediary would authenticate the service provider's performance and determine the level of performance-based incentive to be paid to the service provider. Alternatively, the method may require the patient to confirm and acknowledge the service provider's performance in addition to the intermediary's authentication to determine the level of adherence (performance) and compensation.

Another embodiment of the present invention comprises pre-authorization certification programs that integrate the patient into the authorization process. This is referred to as "patient-integrated pre-authorization certification" and as "doctor-patient mutual accountability pre-certification." In effect, patient-integrated pre-authorization certification involves compensating the service provider for prescribing an educational material as information therapy through the Website to the patient when expensive or risky medical services (such as surgeries or hospitalization) are planned. The patient is financially rewarded for reading about his/her conditions, the planned treatment and treatment alternatives. The patient would then be required to demonstrate his/her knowledge by taking a test so he/she can be qualified to authorize the planned treatment or consult further with his/her service provider about the treatment and ask about alternative treatments or seek a second opinion or refuse the treatment.

Another embodiment of the present invention comprises an enhancement to hospital care management systems by integrating patients into the hospital care process. This is referred to as "patient-integrated hospital care management program." In effect, patients earn financial rewards for performing certain tasks associated with their hospitalizations. One such task is to designate a personal advocate such as a family member or friend. This method of the invention compensates hospitals and attending physicians for prescribing a hospital care plan and discharge instructions through the Website or during admission and at discharge to the patient and his/her advocate. Pre-admission, during the admission and after discharge, the patient and/or advocate would be queried through the Website to demonstrate their knowledge of the hospital care plan and discharge instructions. The Website then asks the patient and advocate to rate the hospital's and attending physician's performance against the hospital care plan. The patient would be asked to declare his/her compliance to hospital care plan and discharge instructions. As a means for the intermediary to authenticate performance, the hospital and attending physician could also be required to access the Website to enter the name of patient's advocate and to indicate the patient's adherence to the hospital care plan, Clearly, the method of the current invention provides a means to incent and motivate the patient to take an active role in managing their medical condition. As a result, the clinical outcome of the patients medical treatment will be enhanced. Thus, the methods of the current invention enhance the quality of medical care by encouraging the patient and medical practitioner through financial rewards and mutual accountability checks and balances to adhere to the scientifically proven best treatment guidelines or preferred methods, healthy behaviors and other performance standards, and by enabling the patient through information therapy to manage the treatment of the medical condition to achieve a higher level of health. By enhancing the quality of medical care and increasing the patients ability to manage their medical condition, the current invention promotes better health and healthcare, which reduces the overall cost of healthcare; while providing an increase in compensation to the medical practitioner, a financial reward to the patient, and cost savings that produces a return on investment to the health plan sponsor. Thus the current invention aligns the interests of these three key stakeholders in a win-win-win arrangement.

Collectively, the descriptions and illustrations presented herein and the terms such as "checks and balances," "declare and confirm," "demonstrate and acknowledge," "doctor-patient mutual accountability," "triangulation," "win-win-win," "mutual accountability partnership," "precision-guided incentives and performance standards," and "alignment of interest" or "AOI" define the invention's unique "interactive" characteristics between medical providers, patients, and health plan sponsors. Hence, the invention can be accurately described as a "web-based interactive provider-patient incentive system."

Figure 3:
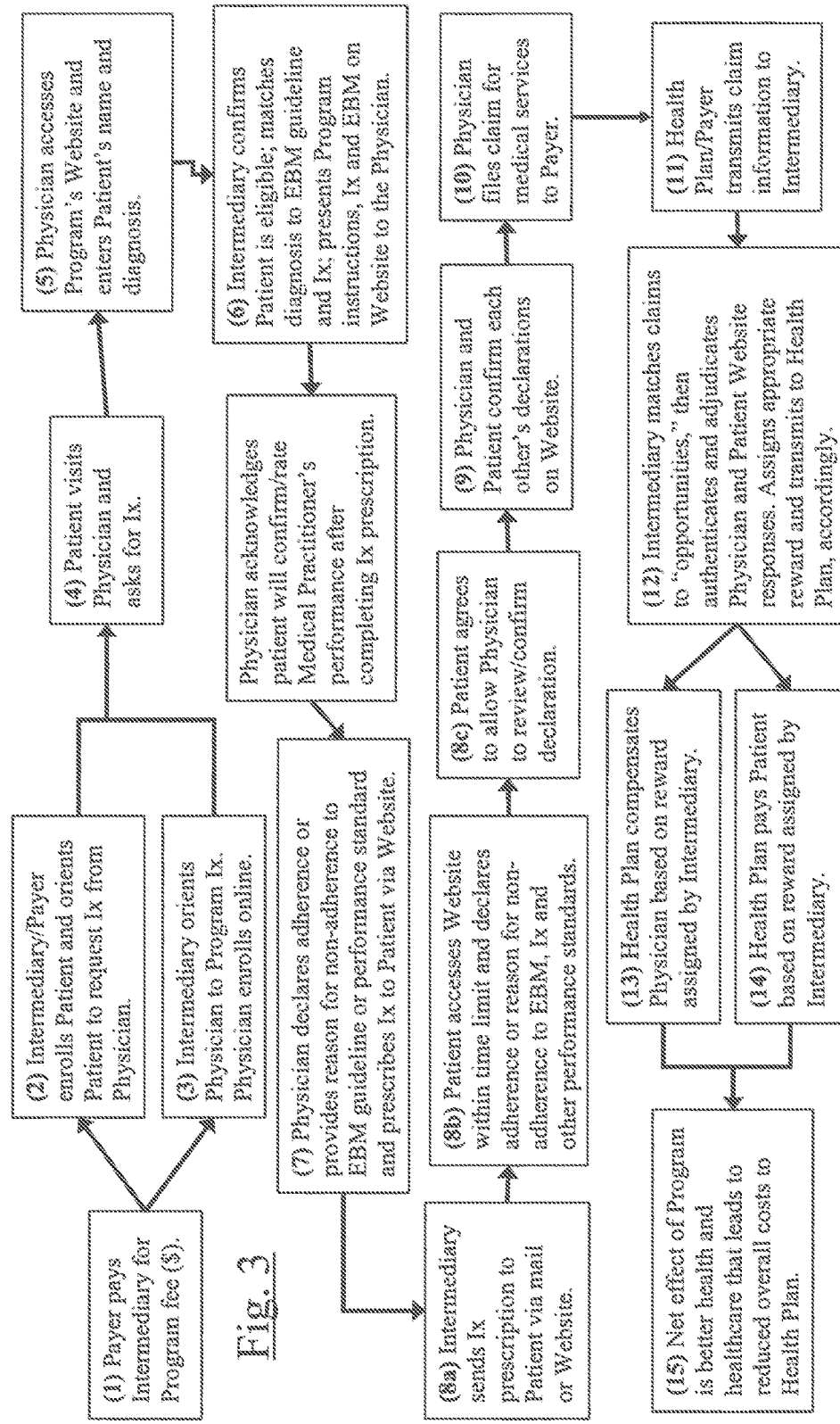
FIG. 3 is a diagrammatic illustration of an Information Therapy (Ix) Program embodiment of the method of the present invention.

FIG. 3 is a diagrammatic illustration of the method of the present invention. The embodiment of FIG. 3 comprises an Information Therapy (Ix) Program. The following discussion provides a step-by-step description intended to illustrate the of combining the method and system of the current invention with the mechanics of the Ix Program process and is not intended to imply that this is the only application of the invention. The following discussion is made in reference to FIGS. 3-16. FIG. 3 illustrates the steps of the process described below. FIG. 4-16 provide exemplary webpage interfaces useful with the present invention.

The example of the current invention discussed below comprises a web-based healthcare delivery incentive method (system or program) that, in this example, is referred to as the Ix Program. The Ix Program described herein involves four parties: health plan sponsor (health insurance companies, self-insured employers, and the Medicare and Medicaid programs) that purchase the Program and underwrite (fund) the cost of health care of persons (beneficiaries/plan members) covered by health insurance (health plan); medical providers (service providers, physicians/doctors, medical practitioners, healthcare providers, and clinicians) who participate in the Program; beneficiaries (patients/consumers) of a health plan that offers the Program; and an intermediary (Informediary) that operates the Program and administers the three agreement between the health plan sponsor, the plan member and the medical provider.

The current invention comprises the following elements: a performance standard or set of performance standards; an Internet website with software applications (Ix Program Website or Website); a computer system operated by the intermediary that hosts the Website and contains certain Ix Program databases; financial rewards; and a system of checks and balances. The performance standards may comprise a set of healthcare treatment standards that have been shown to be effective at improving healthcare rendered by providers, improving the health of beneficiaries, and controlling healthcare costs such as evidence-based medicine (EBM) treatments and information therapy (Ix) prescriptions. The Website contains the Ix Programs proprietary applications that effectuate the system of checks and balances and performance standards or information about performance standards operated by the intermediary. The financial rewards and other types of non-financial incentives are disbursed by the health plan sponsor's administrator (TPA, ASO provider, or health insurance company) to providers and beneficiaries for successfully practicing the Ix Program as determined by the intermediary. The system of checks and balances is established between the medical provider and beneficiary to motivate Ix Program participation and performance standard compliance, and to prevent fraud and use.

With reference to FIG. 3, at Step #1 the health plan sponsors adopt the Ix Program by purchasing the Ix Program from the intermediary (FIG. 3) as a "bolt-on" benefit to the sponsors' health plans. Typically, payment for a "bolt-on" benefit is made on the basis of the number of plan members (consumers/patients/beneficiaries) who are covered by the Ix Program, often referred to as a per-member-per-month (PMPM) access fee.

At Step #2 the beneficiaries enroll, receive orientation, are informed of their opportunity to earn financial or other types of rewards, and are encouraged to request information therapy from their service providers. Beneficiaries may be introduced to and enrolled in the Ix Program through their employment or health insurer. The intermediary and the health plan typically orient beneficiaries (patients) to the Ix Program through written materials, instructional videos, and Website tutorials. One instruction advises beneficiaries to seek care from a participating provider (physician) or to encourage their physician to participate in the Ix Program. Beneficiaries should expect to receive care from his/her provider that meets the performance standard such as EBM treatments and information therapy prescriptions. The Ix Program orientation explains that financial rewards are available to the beneficiary when he/she accesses the Website and appropriately responds on-line (or over the telephone through a telephonic interface to the Ix Program) to information therapy prescribed by his/her physician and/or meets other performance standards.

Figure 4:
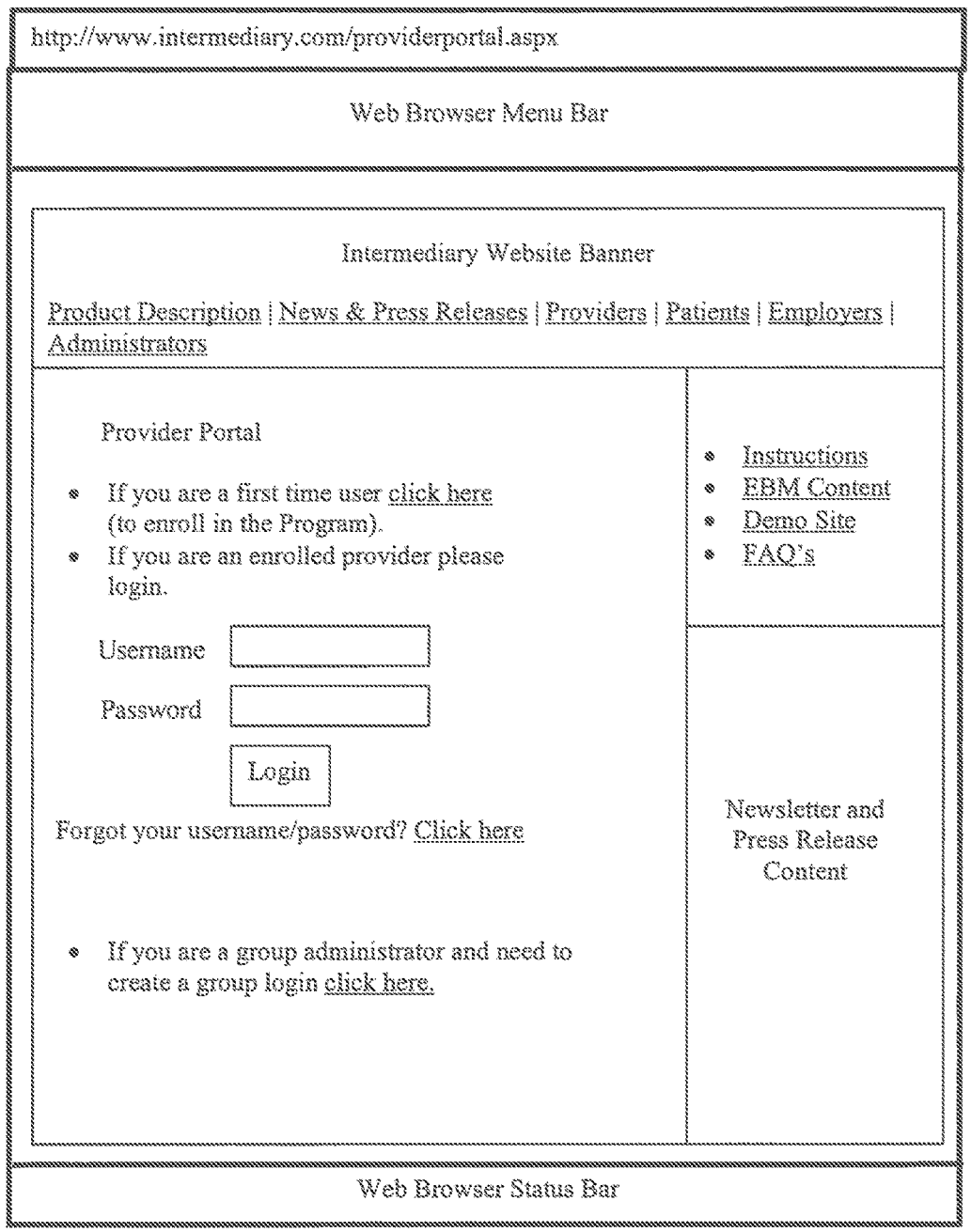
FIG. 4 is an illustrative representation of a webpage used in the method and system of the present invention.

At Step #3 the service providers (physicians/clinicians/medical practitioners) receive orientation and are encouraged to prescribe Ix. An exemplary webpage illustrating the web interface used in Step #3 is shown in FIG. 4. Physicians may be oriented to the Ix Program by the intermediary and health plan in a variety of ways including organized meetings, in-office presentations, mailings, through professional organizations, and faxed notices from the intermediary. Another common means of introduction may involve patients requesting or suggesting that their physicians participate in the Ix Program. The service provider is informed that by practicing the Ix Program, he/she: 1) should have more knowledgeable and compliant patients, 2) will be rendering a higher standard of care, 3) may gain a degree of malpractice risk management, 4) should experience an increase in productivity, 5) should expect a better clinical outcome, and 6) will be appropriately compensated for his/her time and effort. The provider is also informed that the patient will be seeking and expecting information therapy, EBM treatments, and/or other performance standards, and that the patient will be asked to rate the physician's level adherence to the performance standard. Finally, medical providers are informed that participation in the Ix Program: is purely voluntary, even on an encounter-by-encounter basis; involves no costs to set-up or on-going purchases except for Internet access; is designed to be fast and easy to use; and is anti-cook, encouraging medical providers to use their clinical judgment in treating patients, Physicians enroll in the Program online through the Website.

At Step #4 a beneficiary visits a physician and, if he/she wishes, can ask for information therapy and/or other performance standards. When the beneficiary seeks a medical provider participating in the Ix Program or requests services that satisfy the Program's performance standard(s) from his/her physician, it represents the first in a series of checks and balances (nonfinancial or psychological incentives/motivators) between the doctor and patient that encourages positive behavior modification. During an office visit (or other types of medical encounter), the physician renders treatments to the patient and files a normal insurance claim to the patient's health plan for compensation. The physician would typically collect any co-payments or annual deductibles from the patient according to the patient's health plan benefits.

Continuing with Step #5, the physician accesses the Ix Program through the Website. The physician can practice the Ix Program in many ways. Two exemplary methods of practicing the current invention are discussed herein. An exemplary webpage illustrating the web interface used in Step #5 is shown in FIGS. 5 and 6.

Figure 8B:
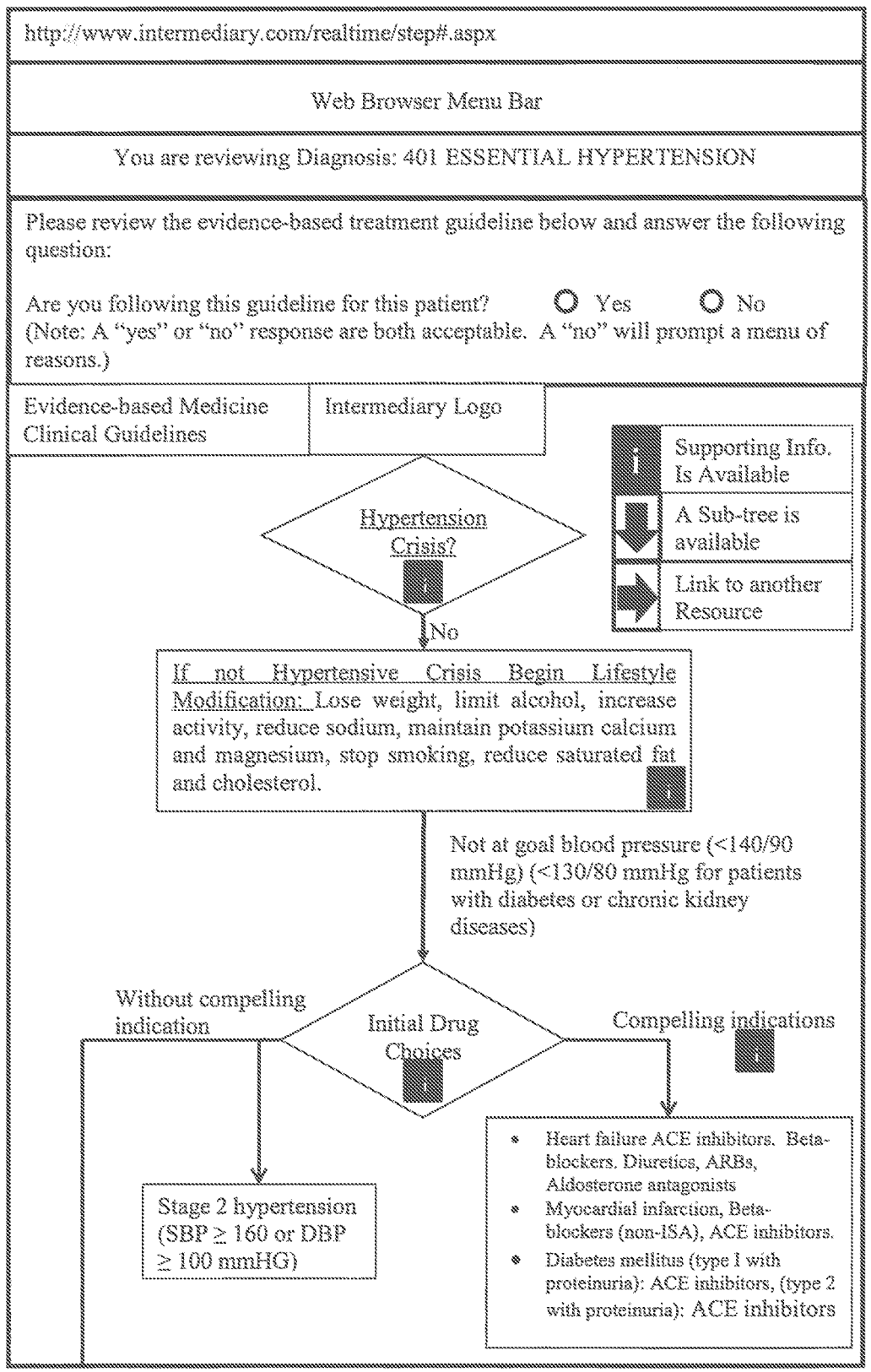
FIG. 8B is an alternative webpage interface designed to guide the service provider through the performance-based standards for a selected diagnosis.
Figure 10:
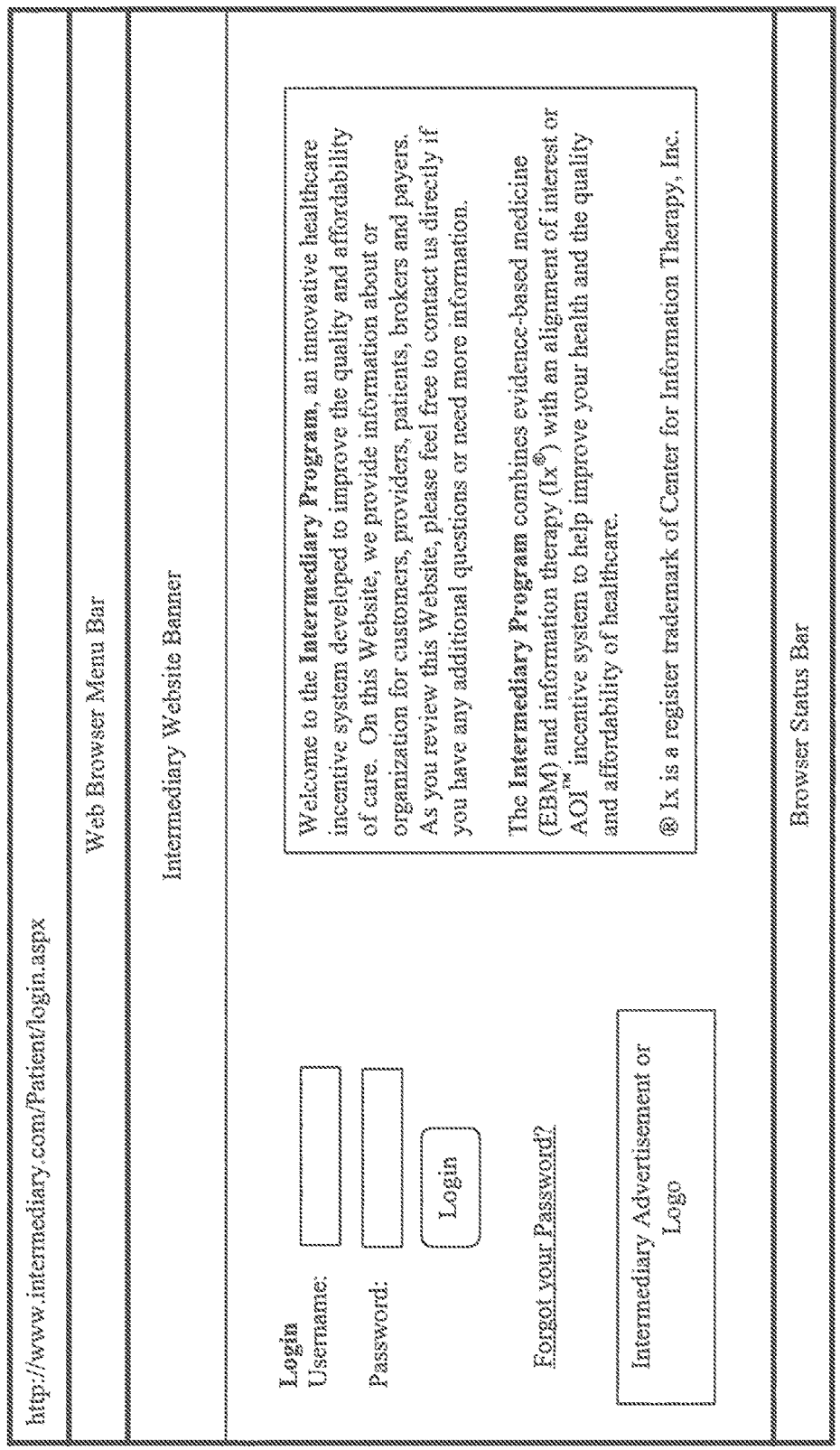
FIG. 10 shows an initial "welcome page" on a patient side of the present method, FIG. 11 an interim webpage used to provide the patient with health information about his/her diagnosis including EBM treatments, recommended care, health maintenance, and/or other performance standards.
Figure 12B:
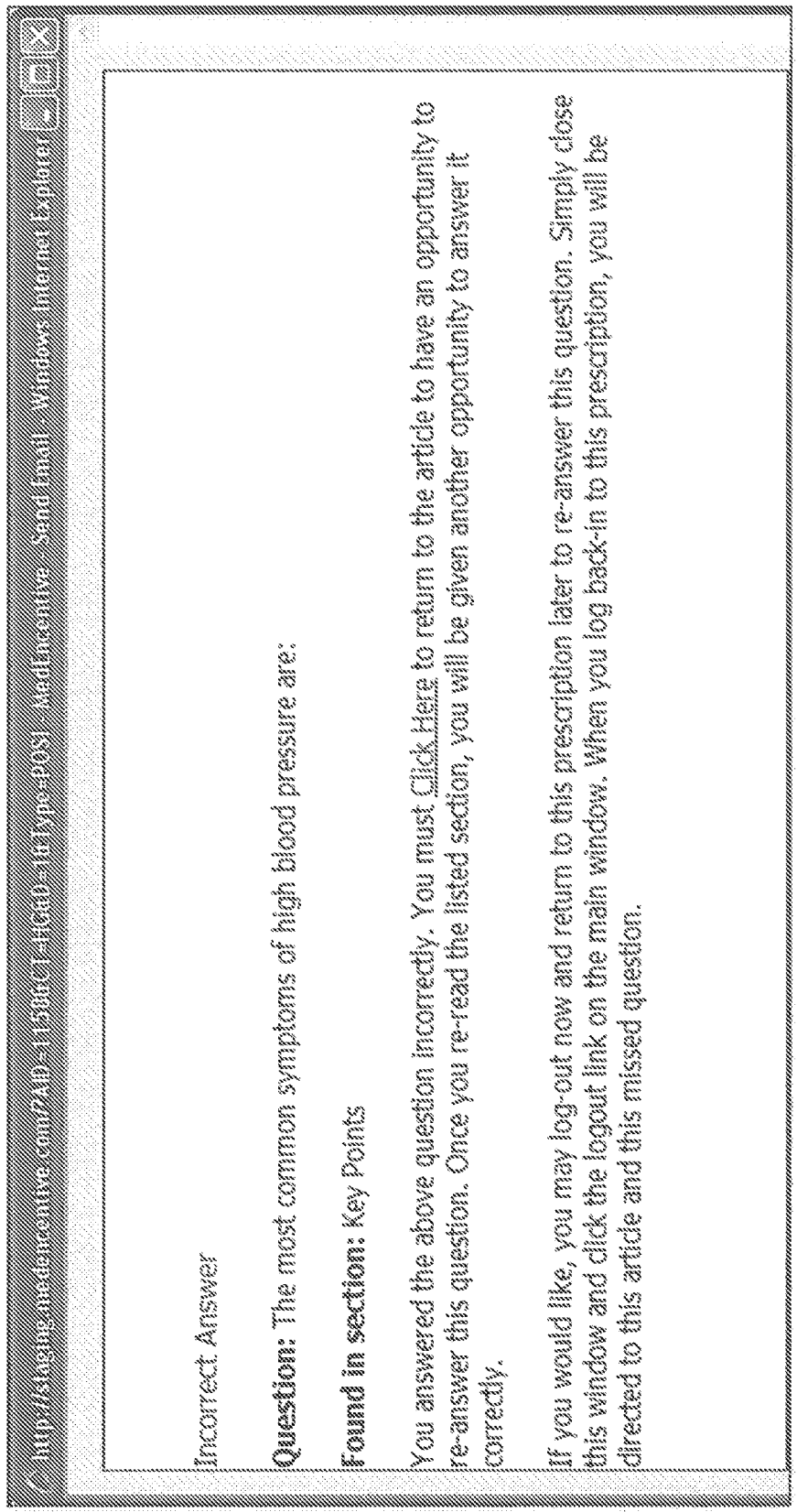
FIG. 12B is an exemplary webpage showing the patient's options after giving an incorrect answer to a web-based test used to test the patient's knowledge of the information therapy prescribed by the service provider.

The physician can initiate the process at the time of service (in the presence of the patient or shortly thereafter) by accessing the Website and using the Point of Service Initiated or POSI real-time version of the Ix Program (FIGS. 4, 5, and 6). On the Website, the physician enters the beneficiary's name or identification number and diagnosis (es) (See FIGS. 5, 6 and 7) and responds to questions and/or performs services at Step #7, as described below. The physician's POSI responses are stored in the intermediary's computer system database for later processing. If the physician forgets or fails to use POSI, then the process can be performed "after-the-fact" using the Claims Initiated or CI version of the Ix Program. FIGS. 8a and 8b are exemplary webpages illustrating the web interface used in Step #5 to evaluate the performance standard provided by the Program in response to the received diagnosis code.

The Website's proprietary software applications determine whether the POSI or the CI version is to be used for each occurrence of care. This is accomplished when the intermediary receives (preferably electronically) a copy from the health plan administrator of the physician's insurance claim for the services rendered during the patient encounter (as mentioned in Step #4, above, and described in Step #10, below). The Website's software applications look to match the claim information to POSI responses by the physician stored in the intermediary's database. If there is a match, then the intermediary orders compensation for the physician as described in Step #12, below. If there is no match, then the intermediary sends an e-mail notification to the physician to practice the Ix Program "after-the-face," This "after-the-fact" process that uses a physician's insurance claim to initiate an e-mail notification to the physician is, in effect, the Claims Initiated or CI version of the Ix Program. The CI version is not depicted in the diagram. However, with the exception of how the processes are initiated, the POSI and CI versions are similar.

At Step #6 the Website supplies EBM treatment guidelines or other types of performance standards, provided guidelines and other types of performance standards exist for the patient's diagnosis). The Website automatically displays EBM treatment guidelines or other types of performance standards to the physician related to the patients diagnosis(es) and/or health plan benefits. In the case of the Ix Program, if a guideline does not exist, then the Website displays medical educational content related to patients diagnosis(es) (FIGS. 8A and 8B). Immediately following Step #6 the service provider acknowledges patient will confirm/rate/concur with/acknowledge service provider's performance after the patient completes an Ix prescription.

Other types of performance standards include but are not limited to: web-based patient-integrated pre-authorization certification of expensive medical services; web-based patient-integrated hospital care management services; web-based drug therapy and pharmacy benefit management programs including e-prescription, therapeutic drug substitution, automated drug interaction warnings, and patient drug education with knowledge assessment; the adoption and use of personal health records; web-based health risk assessment programs; web-based readiness to change programs; web-enabled health screening programs; web-enabled disease management programs; web-based medical education programs; web-enabled wellness and fitness programs such as smoking cessation, weight management and health club usage; web-enabled health monitoring devices; promotion of web-based patient health self-management and therapeutic social networking programs; an integrated advance directive; a medical provider quality and cost transparency program; and or other programs and systems shown or designed to improve the standard of care, promote healthiness and control costs or make health care more affordable.

In Step #7, the physician responds to Website questions designed to initiate an Ix prescription to the patient in the case of the Ix Program model of the invention, if a guideline is displayed on the Website (FIG. 8A and 8B), he physician is asked to answer two or three questions:

a. "Are you following this guideline for this patient? Yes or No" In conjunction with this question, the physician may also be asked to respond to one of the following statements: "I understand that my patient will be asked to confirm or rate my declaration of adherence to this guideline after my patient has been educated about recommended treatments, "Acknowledge," or "I understand that my patient will be asked to concur with my reason for not adhering to this guideline after my patient has been educated about recommended treatments. Acknowledge," (Note: This understanding or agreement can also be included in the service provider Website agreement, which is accepted by the service provider at time of enrollment and/or each time the service provider logs onto the Website.) A physicians answer to this adherence question and his/her acknowledgment of the patient's confirmation together can have a profoundly positive effect on how healthcare is delivered as a result of the current invention. This particular application of the "declare and confirm" method, coupled with patient education, is one of the most powerful checks and balances instigated by the current invention. It is obviously intended to encourage physicians to be adherent to EBM guidelines (or other performance standards) or provide their patients a legitimate reason for non-adherence. It is also intending for patients to be knowledgeable and discriminating about the healthcare they receive. In effect, the health plan is compensating both the physician and patient to participate in this check and balance with the expectation that better healthcare will rendered, and that this will lead to better health and lower costs. It is important to note that one of the most important aspects of the method (invention), which makes it especially attractive to physicians, is its "anti-cookbook medicine" feature. This feature allows physicians to answer this guideline adherence question either "yes" or "no," and still earn full compensation for practicing the method. The reason the health plan sponsor would agree to pay physicians when they answer this question "no" is because the method requires physicians to select a reason for non-adherence to a guideline from a pop-up menu refer to FIGS. 9A and 9B). The physician's reason for non-adherence is stored in the Website's database to be presented to the patient later in the process. The health plan sponsor knows that the physician is aware that his/her reason for non-adherence will be judged by an informed patient. This check and balance solves the issue physicians have had with "cookbook medicine" associated with other pay-for-performance methods that force them to follow a protocol or guideline to be compensated. In fact, this feature encourages physicians to answer "no" when it is appropriate, as tong as the patient is educated as to why a guideline does not fit his/her particular health condition, b. "Which patient education articles do you wish to prescribe to this patient?" The Website attempts to make prescribing educational material fast and easy for the service provider to complete (See FIG. 9c). As shown in FIG. 9c, multiple articles are listed relevancy order to the diagnosis. The service provider simply selects one or more of the articles as information therapy for the patient. The Website also provides a means for the service provider to preview the articles, see which articles he/she prefers for this diagnosis, and see which articles he/she and other service providers have prescribed to the patient in the past. The Program also presents the service provider with a listing of his or her favorite articles or previously prescribed articles. The presentation of information shown in FIG. 9c is based on stored information keyed to the diagnosis code received, the service provider and the patient's history. It should also be noted that this act of prescribing information therapy is extra effort exerted by the physician, which supports the case for additional pay. It should be further noted that many health plan sponsors are not enthusiastic about pay-for-performance programs that compensate physicians more for merely following a recommended treatment guideline because health plan sponsors feet this is what the physician is being paid to do in the first place. This is not the case in the Ix Program's method.

c. "Please rate your patients compliance for this diagnosis: Compliant; Compliance is a non-factor; or No response" or "Compliant. Mostly Compliant; Somewhat Compliant; Mostly Non-compliant; Non-compliant"

This is an optional question that a health plan sponsor can elect to have added to the Ix Program before or after the patient participates in the Ix Program. The health plan sponsor may assign a portion of the patients financial reward based on how the physician answers this question. The service provider's response to this question is not made available to the patient to prevent undermining doctor-patient relations, Once the physician answers these questions, the POSI real-time version of the Ix Program model allows the physician to print an information therapy prescription to hand to the patient before the patient leaves the office. Alternatively, the physician can practice the real-time version at the end of the day for all enrolled beneficiaries, and the intermediary will mail or e-mail the prescriptions to each patient, (In the CI after-the-fact version, all Ix prescription letters are sent by mail or e-mail or text message.) The process continues for the physician when he or she is asked to review and consider patient responses to the Website's questionnaires. These responses are available to the physician through the Website. Responses that indicate the patient is experiencing additional medical issues or distress is sent to the physician as a priority e-mail notice. Since physician participation in the Ix Program is voluntary on a per-occurrence-of-care basis, the act of participation by a physician is an indication that the physician is committed to delivering a higher standard of care, is committed to better patient communication, is interested in patient compliance to recommended treatments, and is willing to have his/her performance judged by his/her patient, Conversely, a physician's non-participation may imply a whole other set of values that may result in patient and health plan sponsor dissatisfaction, The Physicians' level of participation and patient ratings are intended to aggregated over time. Typically, these results will be used first to recognize the service providers with the highest rate of participation and the highest patient ratings. These results can also be made available to physician peer review organizations to provide a degree of due process for the poor performing service providers. Eventually these results are to be made available to health plan sponsor and the general public, thus allowing market forces to provide additional motivation (incentive). But perhaps the most powerful incentive to the physician is his/her desire to prevent his/her patients from thinking he/she practices inferior medicine, In other models of the invention, different types of performance standards can and will be accommodated. However, the process of the service provider (physician/clinician/medical practitioner) being asked to demonstrate or declare adherence or reason for non-adherence to a given performance standard with the understanding that his/her patient will confrim/rate/concur with the service's providers indication of adherence, followed by the patient being asked to learn and demonstration knowledge about the performance standard and, once qualified, being asked to rate the service provider's indication of adherence to the performance standard remains the same for all types of performance standards. The optional process step of physicians rating their patients' adherence to recommended care and the process step of physicians having access to their patients' Website responses (including medical issue warnings) also remain the same for all types of performance standards. The invention is most effectively delivered through the Internet, though it can be delivered by telephone or telephonic interface or other means, provided that the parties and the other elements of the invention remain the same as described herein.

At Steps #8a and 8b of the current invention, the patient receives and responds to the Ix prescription letter/email/text message/notification from the intermediary. In the Ix Program model of the invention, the patient can receive his/her information therapy (Ix) prescription letter from his/her physician as he/she leaves the physician's office or by mail or e-mail. If the physician fails to participate or fails to successfully complete an "Ix opportunity," then the diagnosis listed on the medical service claim for payment submitted by the physician provides the means by which the intermediary's computer system can automatically generate the notification to the patient that informs the patient of his/her chance to participate in the Ix Program for said "Ix opportunity."

The prescription letter directs the patient to access the Website (Step #8b) (See also FIG. 10) where his/her actual prescription will be ready and waiting as a result of the physician's earlier responses to the Website or, when the physician fails to participate in the "Ix opportunity", as a result of the medical service claim for payment submitted by the physician. For each diagnosis entered by the physician associated with this occurrence of care, the beneficiary/patient is asked to do the following on the Website to earn his/her financial reward:

1. Read the health information about his/her diagnosis, including EBM treatments, recommended care, health maintenance, and/or other performance standards (refer to FIG. 11);
2. Answer a questionnaire to indicate or assess his/her knowledge or understanding of the health information (refer to FIG. 12A). If an incorrect answer is received the patient may be presented with the exemplary webpage shown in FIG. 12B which provides the patient with notice that is has answered incorrectly and directs them to the correct answer;
3. Answer a questionnaire about his/her current health status;
4. Answer a questionnaire about his/her compliance to the recommended care (See FIG. 13);
5. Answer a questionnaire about releasing his/her responses to the questionnaires about his/her knowledge or understanding of the health information, his/her health status, and his/her indication of compliance to the recommended care to his/her physician (See FIG. 14);
6. Answer a questionnaire to rate his/her physician's performance against EBM treatments, recommended care or other performance standards as:
   Consistent;
   Mostly Consistent;
   Somewhat Consistent;
   Mostly Inconsistent;
   Inconsistent
   or review any reasons recorded by the physician for non-adherence to the treatment guideline or other performance standards and answer a questionnaire to express a qualified opinion in regards to the physician's reason for non-adherence (See FIG. 15); and
7. Alternatively, elect to authorize the release of the physicians rating of his/her compliance to recommended care (if the physician is asked this question), Depending upon how or if the patient answers these questions, he/she scores points toward a financial reward for this occurrence of care (Ix opportunity). Once his/her point total reaches a required threshold, the Website presents a voucher (See FIG. 16) that notifies the patient that he/she has earned the financial reward offered by his/her purchaser/payer. (Note that the physician rating questionnaires can be made even more objective by asking the patient to qualify his/her rating response. For instance, if the patient's diagnosis is hypertension and the patient rated the physicians performance as "Consistent," then the Program can drill down by asking the patient if the physician informed him/her about controlling salt intake or being sure to stay on his/her medication or that he/she should check his/her blood pressure regularly. Again, this provides a more objective means of rating physicians than the prevalent use of subjective satisfaction surveys)

The patient's participation and authorization to release his/her responses to the questionnaires to his/her physician is an indication that the patient wants his/her physician to know he/she understands how to self-manage his/her medical condition and is committed to being compliant to recommended care and healthy behaviors or is providing a reason he/she is willing to share with his/her physician as to why he/she is not being compliant. In the process, the patient learns valuable information that he/she may have not known or did not understand or forgot to ask the physician that can be used to better self-manage his/her health. In addition, the patient gains the peace of mind that he/she is receiving EBM treatments or other standard of performance from his/her physician. Finally, the patient receives a financial reward for his/her effort and healthy behavior.

As with service providers (physicians/doctors/clinicians/medical practitioners/healthcare providers), other types of performance standards can and will be accommodated by the current invention. However, the process of the patient (beneficiary/health plan member) being asked to demonstrate or declare his/her health literacy and adherence (or provide a reason for non-adherence) to a given performance standard, agreeing to allow the physician to review/confirm/rate/acknowledge his/her health literacy and indication of adherence to the performance standard(s), and the confirming/rating/concurring with/acknowledging the physicians declaration or demonstration of the adherence or reason for non-adherence to performance standards remains the same for all types of performance standards. The optional process step of physicians rating their patients adherence to recommended care and the process step of physicians having access to their patients' Website responses (including medical issue warnings) also remain the same for all types of performance standards, Referring still to FIG. 3, in Step #8c the patient agrees to allow the service provider to review/confirm the patient's responses to the queries posed the patient in Steps 8a, and 8b.

In Step #9, the physician and patient confirm each other's performance using the Internet application. As mentioned in reference to Steps #7 and #8, the method asks the physician and patient to review and confirm each other's declarations or demonstration of adherence or reason for non-adherence to an EBM benchmark and/or other performance standards. Both parties are aware they must agree or acknowledge that the other party can and may confirm/rate/acknowledge/concur with their declaration or demonstration of adherence or reason for non-adherence to the EBM benchmark and/or other performance standards in order to earn the financial rewards offer through the Ix Program. Physicians do not want their patients to think or learn they practice inferior medicine. Conversely, patients (especially patients with chronic conditions that have close relationships with their physicians) do not want their physicians to think they are health illiterate or non-compliant with recommended treatments and health behaviors. As a result, physicians and patients are motivated to please one another by gaining health literacy, adopting healthy behaviors, following recommended treatments and delivering high quality healthcare. Furthermore, since both parties are aware that their responses are being recorded and stored by an independent third party (the intermediary), and that this information could be reported to the health plan and, in the case of physicians, the general public, then both parties are even more motivated to gain health literacy, adopt healthy behaviors, follow recommended treatments and deliver high quality healthcare. In effect, the method's processes that combine the attributes of financial (behavioral economics and non-financial (health psychology) motivators (i)centives) creates powerful "checks and balances" ("mutual accountability") that encourages a higher standard of care and healthier behavior that leads to lower costs.

At Step #10, the physician files a health insurance claim with the health plan. As mentioned with reference to Steps #4 and #5, the normal filing of an insurance claim by the physician for medical services covered by the Ix Program can occur before, concurrently, or after the method is practiced by the physician. (An insurance claim contains all the information needed by the Ix Program's web-based software applications to complete the process.) The claim must be filed within a certain time limit established by the health plan sponsor and the intermediary. If a physician does not access the Website and practiced the POSI real-time version of the method by the time the physician's claim reaches the intermediary, then the CI after-the-fact version of the method will send an e-mail notification to the physician. This is referred to as a "CI opportunity." The physician will have a time limit to respond to a "CI opportunities." If a "CI opportunity" expires, the health plan sponsor and the intermediary may elect to send the patient an Ix prescription based on the diagnosis(es) listed on the insurance claim submitted by the physician. This allows patients to gain valuable health information and earn a financial reward, even when their physicians fail to participate in the Program. This process is referred to as "system-generated information therapy." To encourage physician participation while insuring patients are not deny the opportunity to participate in the Ix Program when their physician fail/forget to participate, the health plan sponsor and the intermediary can offer patients larger financial rewards for "physician generated Ix" than for "system-generated Ix."

Step #11 comprises the health plan/payer sending claim information to the intermediary. A plan administrator can be a third party administrator (TPA) or a health insurer's administrative services only (ASO) contracted be a self-insured employer (t)e health plan sponsor) or the health insurer (the health plan sponsor) in the case of fully-insured employers and individuals or government agencies. The plan administrator forwards all insurance claims to the intermediary. Preferably, claims are sent automatically and electronically on a daily basis, using industry standard electronic data interchange (EDI) interfaces and formats. Once downloaded into the intermediary's computer, the Ix Program's software applications sort the data to find claims containing covered medical services (applicable medical services) rendered to beneficiaries covered by the Ix Program.

Step #12 comprises the intermediary matching claims to "opportunities," then authenticates and adjudicates physician and patient Website responses, and directs financial compensation and other reward notifications to the health plan/payer. As described with reference Step #5, above, the intermediary uses the Website's software applications to match insurance claims to physician POSI responses stored in the intermediary's database. If there is a match, the intermediary sends an (electronic) authorization/directive to the plan administrator to compensate the physician (and sends the information therapy prescription to the patient as described in Step #7, above). Since the POSI real-time version is the preferred method, the intermediary can select a premium or highest rate of compensation for the physician. If the intermediary cannot match an applicable insurance claim to a POSI, then the Claim Initiated or CI version of the method sends an email notification to the physician. If the physician responds to the "CI Opportunity" and successfully practices the method within the allotted time, then the intermediary sends an (electronic) authorization/directive to the plan administrator to compensate the physician (and sends the information therapy prescription to the patient as described in Step #7, above). Since the POSI real-time version is the preferred method, the intermediary can select a tower rate of compensation for the physician practicing the CI after-the-fact version of the method. The Website applications track patient information therapy and other performance standards responses. When a patient successfully completes an Ix prescription or other performance standard through the Website (or over the telephone or by other means), then the Ix Program's software applications adjudicate the patient's reward and the intermediary sends an authorization/directive to the plan administrator to pay the assigned reward to the patient. If the physician or the patient do not independently and individually (or perhaps dependently and collectively) respond to their respective "Ix opportunities" within established timeframes, then the Ix Program software applications close-out each opportunity accordingly, and the physician and patient do not earn financial compensation or rewards. All of these events are recorded and stored for future consideration by the intermediary and the health plan.

Step #13 comprises the health plan sponsor, through the plan administrator, compensating the physician. When the plan administrator receives the payment authorization/directive from the intermediary, the plan administrator reimburses the physician one of multiple levels of compensation according to the contracted terms between the health plan or intermediary and the physician. Alternatively, the health plan sponsor may assign the physician and payment function to the intermediary. In this case, the intermediary makes payments to physicians from funds supplied by the health plan sponsor. In the current invention and under the terms of the agreement between the health plan or intermediary and the service provider, varying amounts of compensation can be paid for a variety of performances standards.

At Step #14 the health plan sponsor, through the plan administrator, pays the beneficiary a financial reward. When the plan administrator receives the payment authorization/directive from the intermediary, the plan administrator pays the patient one of multiple levels of compensation according to the benefit established by the health plan sponsor in consultation with the intermediary and the performance standard achieved by the patient. Alternatively, the health plan sponsor may assign the payment function to the intermediary. In this case, the intermediary makes payments to patient from funds supplied by the health plan sponsor, Step #15 comprises the health plan sponsor realizing a cost savings. Though this is not an actual step in the process, the intended by-products of the method is a higher standard of care (featuring EBM treatments and information therapy) and healthier behaviors that studies have shown leads to lower costs. In the current invention, the health plan sponsor agrees to compensate medical providers and patients to "declare and confirm" their adherence to performance standards, and to compensate the into mediary for operating the system and authenticating physicians and patients' declarations and confirmations. More specifically, the health plan sponsor agrees, in order to achieve cost containment as a result of better health and healthcare, to:

1. compensate the medical provider (physician and hospital) for accessing the Website to:
    a. declare or demonstrate adherence or providing a reason for non-adherence to evidence-based treatments and other provider performance standards;
    b. agree or acknowledge the provider's patients will confirm/rate/concur with/acknowledge his/her declaring or demonstrating adherence or providing a reason for non-adherence to evidence-based treatments and other performance standards after patients demonstrate they understand the treatments on the Website;

c. prescribe information therapy and other performance standards to the patient;
d. optionally, rate his/her patients' level of adherence to recommended herein; and
e. responding to his/her patients' responses to the Website's questionnaires and inputs to include warnings of medical issues 2. financially reward patients (benficiaries) for accessing the Website to:
a. read prescribed educational material as information therapy;
b. declare or demonstrate (by tests) his/her understanding of the educational material (health literacy), especially as it pertains to self-managing his/her health and the recommended treatments;
c. declare or demonstrate adherence or providing a reason for non-adherence to the recommended treatments, healthy behaviors and other related performance standards;
d. report his/her health status;
e. agree to allow his/her medical providers to review/rate/acknowledge his/her health literacy, health status, and indication of adherence responses;
f. confirm/rate/concur with/acknowledge his/her medical providers' declaration or demonstration of adherence or reason for non-adherence to evidence-based treatments and other performance standards;

3. compensate the intermediary for:
a. operating the invention's incentive system to include the Program's Website and/or other technologies;
b. developing and maintaining the associated software applications and databases;
c. providing and/or interfacing the performance standards supplied by vendors;
d. the performance standards;
e. adjudicating and authenticating medical providers and patients' declarations, confirmations, demonstrations, and acknowledgments of adherence to performance standards;
f. adjudicating and authenticating medical providers and patients' agreements and acknowledgments to allow the other party's declarations, confirmations, demonstrations, and acknowledgments of adherence to performance standards;
g. directing and/or affecting service provider and patient compensation and financial rewards;
h. tracking, reporting, and analyzing results; and
i. recommending refinements to the Program to include "precision guided incentives and performance standards (adjustments to and expansion of the incentives and performance standards).

By combining the parties and elements of the method in the manner described herein, the invention "triangulates" the interests of healthcare's key stakeholders the health plan, the medical provider and the consumer/patient—in a win-win-win arrangement. By attaining this unique "triangulation" among these key stakeholders, the invention achieves the goals of better health and better and more affordable healthcare. Thus the invention can be described as a "web-based healthcare incentive system" that creates an "alignment of interests" and a "state of equilibrium" and a "mutual accountability' partnership" among the key stakeholders to achieve the goats of better health and better and more affordable health care. As a result, the invention is better described as an "alignment of interest" or "AOL" program as opposed to the more familiar pay-for-performance program descriptor.

Other embodiments of the current invention wilt be apparent to those skilled in the art from a consideration of this specification or practice of the invention disclosed herein. However, the foregoing specification is considered merely exemplary of the current invention with the true scope and spirit of the invention being indicated by the following claims.

What is claimed is:

1. A method for managing a patient's health and healthcare costs, the method comprising:
authenticating an electronic device to a computer that stores a patient account record corresponding to a patient identification;
commanding the computer to generate and transmit a unique patient webpage for display on the electronic device using data from the patient account record; wherein the patient webpage comprises an opportunity to earn a financial reward associated with a medical service that is unique to the patient account record, the opportunity comprising a healthcare provider name and a patient diagnosis associated with a date of service, an expiration date assigned to the opportunity by the computer, and a patient session link to instruct the computer to generate and display an information therapy prescription, a patient knowledge exam, a patient declaration link, a patient agreement link, and a patient rating link;
displaying the information therapy prescription at the electronic device;
displaying the patient knowledge exam on the electronic device, the knowledge exam comprising a plurality of questions related to the information therapy prescription and selected by the computer from a question database;
receiving input signals from the electronic device, the signals comprising answers to the plurality of questions;
creating and displaying a new webpage when an incorrect answer is received directing the patient to a question with the incorrect answer and a portion of the information therapy prescription containing a correct answer;
activating the patient declaration link to transmit a signal from the electronic device to indicate a patient declaration of adherence or reason for non-adherence to the information therapy prescription;
receiving the signal from the patient declaration link, the signal comprising an answer to the patient declaration of adherence or reason for non-adherence to the information therapy prescription;
amending the patient account record to indicate a patient declaration of adherence or reason for non-adherence to the information therapy prescription;
activating the patient agreement link to transmit a signal used to amend the patient account record to indicate a patient agreement to release the patient's answers to the plurality of questions and the declaration of adherence or reason for non-adherence to the information therapy prescription and to the healthcare provider;
activating the patient rating link to transmit a signal indicative of the patient's answers to the rating of the healthcare provider; and
thereafter, the computer authorizes disbursement of the financial reward to the patient.

2. The method of claim 1 wherein the electronic device comprises an Internet or application enabled device.

3. The method of claim 1 wherein authenticating the electronic device to the computer comprises receiving the patient identification and an authentication factor both corresponding to the patient account record at the computer.

4. The method of claim 1 wherein the electronic device and the computer communicate via the Internet.

5. The method of claim 1 wherein the patient web page comprises a plurality of opportunities to earn financial rewards each comprising an entry on the patient account record comprising the healthcare provider name and the patient diagnosis associated with a date of service, the expiration date of the opportunity assigned by the computer, and the patient session link.

6. The method of claim 1 further comprising before displaying the information therapy prescription and the knowledge exam on the electronic device, the computer automatically processes the patient account record to determine if the expiration date assigned by the computer has passed, thereafter the computer does not authorize disbursement of the financial reward to the patient if the computer determines the expiration date has passed.

7. The method of claim 1 further comprising creating and sending an electronic mail message or postal notice to the patient of the opportunity to earn a financial reward associated with a medical service before displaying the unique patient webpage.

8. The method of claim 7 wherein the electronic mail message comprises an active link to the unique patient webpage.

9. The method of claim 1 further comprising the computer establishing a threshold dwell time for the electronic device to display the information therapy prescription and measuring the dwell time, authorizing disbursement of the financial reward if the measured dwell time meets or exceeds the threshold dwell time.

10. The method of claim 1 wherein the information therapy prescription comprises an educational material selected by the computer based on the patient diagnosis.

11. The method of claim 1 wherein the patient's rating of the healthcare provider is aggregated with ratings from a plurality of patients and transmitted by the computer to the healthcare provider as a composite performance rating.

12. The method of claim 11 wherein the computer uses the composite performance rating to determine a level of compensation to the healthcare provider.

13. The method of claim 1 further comprising instructing a health plan to disburse the financial reward to the patient.

14. The method of claim 12 further comprising instructing a health plan to disburse the financial reward to the healthcare provider.

15. A computer implemented method for managing health and healthcare costs, comprising executing on a processor the steps of:
creating a financial reward opportunity record for a patient based on a patient identifier and a medical diagnosis code associated with a medical service rendered by a healthcare provider to the patient received in a first electronic message;
assigning a time limit to the financial reward opportunity record;
linking an information therapy selected from an information therapy database to the financial reward opportunity record;
linking a randomly selected query related to the information therapy from a plurality of queries stored in a query database to the financial reward opportunity record;
receiving a second electronic message comprising the patient identifier and requesting access to the financial reward opportunity;
in response to the second electronic message, accessing the financial reward opportunity record to create and transmit a patient session webpage comprising the medical diagnosis code, the selected information therapy, the query, and an active link to generate a third electronic message comprising a patient declaration of adherence or reason for non-adherence to the information therapy, a patient answer to the query, and a patient agreement to release the patient answer and the patient declaration of adherence or reason for non-adherence transmitted to the healthcare provider;
receiving and processing the third electronic message to write the patient declaration of adherence or reason for non-adherence, the patient answer, and the patient agreement to release to a patient record and to confirm receipt of the third electronic message prior to the time limit; and
thereafter authorizing disbursement of the financial reward to the patient.

16. The method of claim 15 further comprising processing the patient answer to the query and creating and displaying a new webpage when the patient answer is incorrect, the new webpage comprising the query for which the patient answer was given and at least a portion of the information therapy containing a correct answer to the query.

17. The method of claim 15 further comprising:
receiving a healthcare provider identification at the computer from a provider electronic device;
processing the healthcare provider identification to create and transmit a healthcare provider webpage for display on the provider electronic device, the healthcare provider webpage comprising a plurality of fields to receive data from a healthcare provider containing the patient identifier and the medical diagnosis code;
wherein the computer receives the patient identification and the medical diagnosis code and generates a healthcare provider prescription page for display on the provider electronic device, the prescription page comprising plurality of active links for the healthcare provider to select an offer of a healthcare provider financial compensation, a healthcare provider performance standard, a patient performance standard and information therapy corresponding with the medical diagnosis code, and an expiration date assigned to the offer by the computer;
the computer processes the data received from the prescription page and generates a unique declaration page corresponding to the patient identification and the medical diagnosis code comprising a plurality of active links to receive and transmit data from the provider electronic device to the computer comprising a healthcare provider declaration of adherence or reason for non-adherence to the healthcare provider performance standard, a healthcare provider acknowledgment that the patient will rate or confirm the healthcare provider declaration of adherence or reason for non-adherence, a patient performance standard and information therapy prescription, and an agreement to confirm and acknowledge the patient declaration of adherence or reason for non-adherence;
the computer receives the data from the declaration page and automatically processes the data to determine if the healthcare provider has declared adherence to the healthcare provider performance standard or provided a reason for non-adherence that corresponds to at least one reason for non-adherence from plurality of preselected reasons for non-adherence stored in a database at the computer; and the computer issues a command signal to order disbursement of the healthcare provider financial incentive to the healthcare provider based upon authentication of the data received from the prescription page and the healthcare provider declaration of adherence or authorized reason for non-adherence, if the expiration date has not passed.

18. The method of claim 17 further comprising processing data received from the prescription page to generate the patient session webpage.

19. The methods of claim 17 wherein the command signal is transmitted to a health plan computer, and comprises an order to disburse the service provider financial incentive comprising monetary compensation to the service provider.

20. The method of claim 15 further comprising before transmitting the patient session webpage, the computer automatically processes the financial opportunity reward record to determine if the time limit has passed, thereafter the computer does not authorize disbursement of the financial reward to the patient if the computer determines the time limit has passed.

* * * * *